United States Patent
Gregoire et al.

(10) Patent No.: US 9,778,234 B2
(45) Date of Patent: Oct. 3, 2017

(54) GENERATION AND ANALYSIS OF CHEMICAL COMPOUND LIBRARIES

(71) Applicants: California Institute of Technology, Pasadena, CA (US); The Regents of the University of California, Oakland, CA (US)

(72) Inventors: John M. Gregoire, Sierra Madre, CA (US); Jian Jin, Berkeley, CA (US); Kevin S. Kan, Pasadena, CA (US); Martin R. Marcin, Simi Valley, CA (US); Slobodan Mitrovic, Pasadena, CA (US); Paul F. Newhouse, Pasadena, CA (US); Santosh K. Suram, Pasadena, CA (US); Chengxiang Xiang, Costa Mesa, CA (US); Lan Zhou, Pasadena, CA (US)

(73) Assignees: California Institute Of Technology, Pasadena, CA (US); The Regents of the University of California, Oakland, CA (US)

( * ) Notice: Subject to any disclaimer, the term of this patent is extended or adjusted under 35 U.S.C. 154(b) by 515 days.

(21) Appl. No.: 14/336,638

(22) Filed: Jul. 21, 2014

(65) Prior Publication Data
US 2015/0042352 A1 Feb. 12, 2015

Related U.S. Application Data

(60) Provisional application No. 61/856,559, filed on Jul. 19, 2013, provisional application No. 61/974,034, (Continued)

(51) Int. Cl.
*G01N 27/403* (2006.01)
*G01N 33/00* (2006.01)
(Continued)

(52) U.S. Cl.
CPC .......... *G01N 33/00* (2013.01); *G01N 27/305* (2013.01); *G01N 27/403* (2013.01);
(Continued)

(58) Field of Classification Search
CPC .. G01N 33/4836; G01N 21/63; G01N 27/327; G01N 27/3272; G01N 27/403
See application file for complete search history.

(56) References Cited

U.S. PATENT DOCUMENTS

2002/0014413 A1* 2/2002 Symons ................. G01N 27/49
  205/81
2012/0100627 A1* 4/2012 Bekki ................... G01N 27/305
  436/149

OTHER PUBLICATIONS

Derwent English language absract of Huang et al. CN 101660121 A, patent published Mar. 3, 2010.*
(Continued)

*Primary Examiner* — Alexander Noguerola
(74) *Attorney, Agent, or Firm* — Gavrilovich, Dodd & Lindsey LLP

(57) ABSTRACT

Various samples are generated on a substrate. The samples each includes or consists of one or more analytes. In some instances, the samples are generated through the use of gels or through vapor deposition techniques. The samples are used in an instrument for screening large numbers of analytes by locating the samples between a working electrode and a counter electrode assembly. The instrument also includes one or more light sources for illuminating each of the samples. The instrument is configured to measure the photocurrent formed through a sample as a result of the illumination of the sample.

14 Claims, 12 Drawing Sheets

Related U.S. Application Data filed on Apr. 2, 2014, provisional application No. 61/979,372, filed on Apr. 14, 2014.

(51) Int. Cl.
   *G01N 33/483*     (2006.01)
   *G01N 27/30*      (2006.01)
   *G01N 21/63*      (2006.01)

(52) U.S. Cl.
   CPC ......... *G01N 33/4836* (2013.01); *G01N 21/63* (2013.01); *G01N 2033/0095* (2013.01)

(56) References Cited

OTHER PUBLICATIONS

Derwent Englsih langauge absract of Liu et al. CN 1844000 A, patent published Oct. 11, 2006.*
Kylberg et al., "Screening of Photoactive Dyes on TiO2 Surfaces Using Scanning Electrochemical Microscopy," J. Phys. Chem. C 2012, 116, 17384-17302.*

* cited by examiner

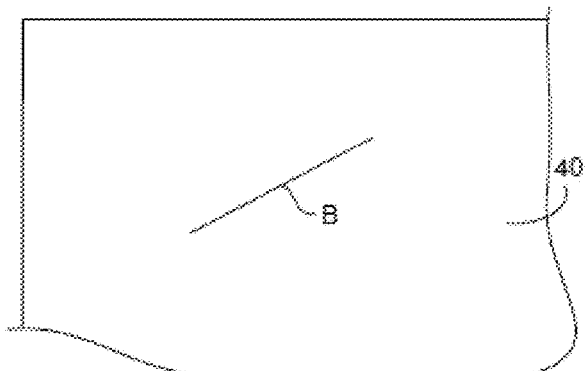
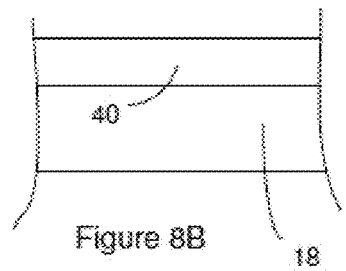
Figure 8A
Figure 8B
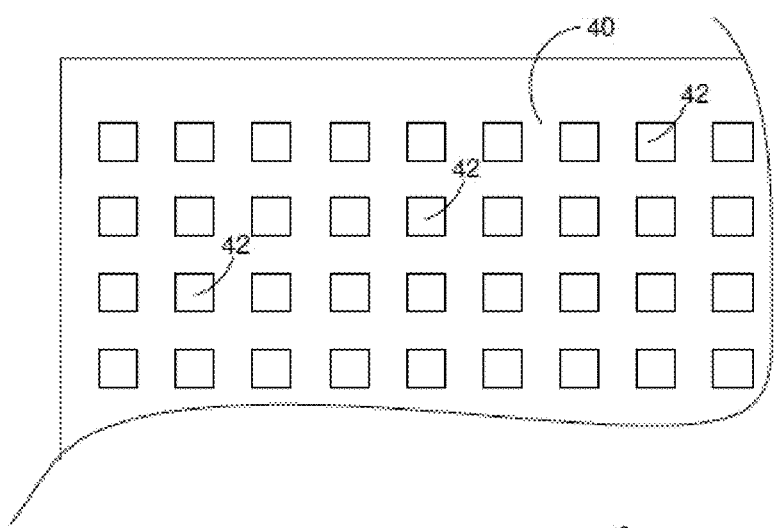
Figure 8C
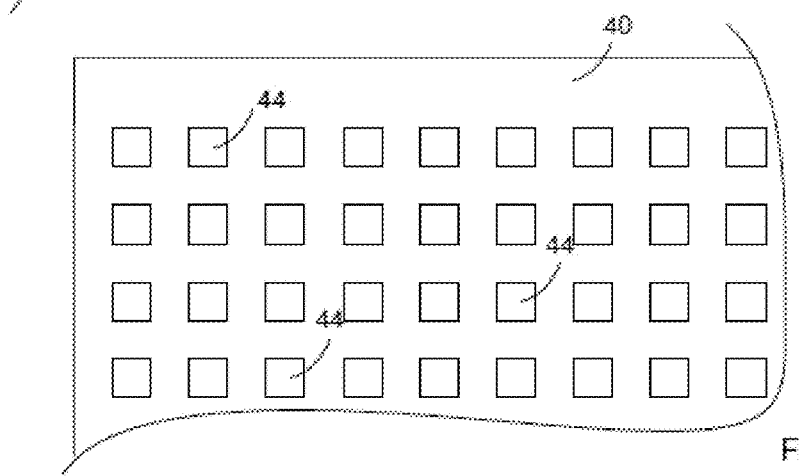
Figure 8D

GENERATION AND ANALYSIS OF CHEMICAL COMPOUND LIBRARIES

CROSS REFERENCE TO RELATED APPLICATIONS

This application claims the benefit of U.S. Provisional Patent Application 61/974,034, filed on Apr. 2, 2014; and also claims the benefit of U.S. Provisional Patent Application 61/856,559, filed on Jul. 19, 2013; and also claims the benefit of U.S. Provisional Patent Application 61/979,372, filed on Apr. 14, 2014; each of which is incorporated herein in its entirety for any and all purposes.

STATEMENT REGARDING FEDERALLY SPONSORED RESEARCH OR DEVELOPMENT

This invention was made with government support under DE-SC0004993 awarded by the US Department of Energy. The government has certain rights in the invention.

FIELD

The present invention relates to material libraries and more particularly to generation and screening of material libraries.

BACKGROUND

A variety of devices convert light into a different form of energy. Examples of these devices include, but are not limited to, solar fuel generators and photovoltaic devices such as solar cells. These devices typically include one or more light absorbers. Light absorbers are materials in which incident photons can excite electron-hole pairs within the light absorber. There are a tremendous number of materials that can serve as these light absorbers. However, the light absorbers have different valence band energies, different conduction band energies, and different band gaps. Further, these materials are often in contact with one or more electrical contacts or solution contacts. The different materials can be more suitable for use with one type of metal contact or solution contact than with another type of metal contact or solution contact. As a result, it is often desirable to identify the light absorbers that are most suitable for use with a particular application. Since the number of light absorber candidates is so large, there is a demand for technologies that can be employed to efficiently generate and screen large numbers of light absorber candidates.

SUMMARY

An instrument includes samples located between a working electrode and a counter electrode assembly arranged such that the distance between the working electrode and the counter electrode assembly is less than 10 mm. The samples each include one or more analytes. The instrument also includes one or more light sources that each act as a source of one or more light beams that each illuminates one or more of the samples. The instrument can include electronics that measure one or more parameters that result from a photocurrent through each of the samples in response to the sample being illuminated by the one or more light beams. In some instances, each of the different samples includes a different light absorber.

An instrument includes samples located between a working electrode and a counter electrode assembly. The samples each include one or more analytes. An electrolyte is positioned between the working electrode and the counter electrode assembly. The electrolyte includes a redox couple. In some instances, the redox couple has a well-defined Nernstian potential with exchange current density of at least 1 mA cm$^{-2}$ for typical electrode materials such as platinum, gold and/or copper. In some instances, the redox couple can have an exchange current density of at least 1 mA cm$^{-2}$, 10 mA cm$^{-2}$, or 100 mA cm$^{-2}$, for one or more of the counter electrodes and/or for one or more of the samples. The instrument also includes one or more light sources that each act as a source of one or more light beams that each illuminate one or more of the samples. The instrument can include electronics that measure one or more parameters that result from a photocurrent through each of the samples in response to the sample being illuminated by the one or more light beams. In some instances, each of the different samples includes a different light absorber.

A method of forming samples on a substrate includes sputtering a layer of material onto a substrate using multiple different anions and multiple different cations in a sputtering chamber. The sputtering is performed such that the layer of material incorporates the multiple different anions and the multiple different cations. In some instances, the layer of material includes multiple different analytes that are each a light absorber. The substrate and layer of material can optionally serve as the working electrode and samples in an instrument for measuring one or more parameters that result from generation of a photocurrent by each sample in response to the sample being illuminated a light beam.

A method of forming a sample on a substrate includes generating a gel on the substrate. The method also includes using the gel to generate a solid layer of material on the substrate. The solid layer of material includes an analyte. The method also includes using the solid layer of material as one of multiple samples included in an instrument for measuring a parameter that result from generation of a photocurrent by the sample in response to the sample being illuminated a light beam.

BRIEF DESCRIPTION OF THE FIGURES

FIG. 1A is a bottom view of a portion of a counter electrode assembly.

FIG. 1B is a topview of a portion of a working electrode assembly.

FIG. 1C illustrates an instrument that includes the counter electrode assembly of FIG. 1A and the counter electrode assembly of FIG. 1B.

FIG. 2A is a bottom view of a portion of the counter electrode assembly.

FIG. 2B is a topview of a portion of a working electrode assembly.

FIG. 2C illustrates an instrument that includes the counter electrode assembly of FIG. 2A and the counter electrode assembly of FIG. 2B.

FIG. 3A is a bottom view of a portion of the counter electrode assembly.

FIG. 3B is a topview of a portion of a working electrode assembly.

FIG. 3C illustrates an instrument that includes the counter electrode assembly of FIG. 3A and the counter electrode assembly of FIG. 3B.

FIG. 3D illustrates an instrument that includes the counter electrode assembly of FIG. 3A and the counter electrode assembly of FIG. 3B.

FIG. 4A is a bottom view of a portion of the counter electrode assembly.

FIG. 4B is a topview of a portion of a working electrode assembly.

FIG. 4C illustrates an instrument that includes the counter electrode assembly of FIG. 4A and the counter electrode assembly of FIG. 4B.

FIG. 8A through FIG. 8F illustrate a possible method for generating a working electrode assembly as illustrated in the instrument of FIG. 1B, FIG. 2B, and FIG. 3B. FIG. 8A is a topview of an assembly precursor having a gel precursor layer on a working electrode.

FIG. 8B is a cross section of the assembly precursor shown in FIG. 8A taken along the line labeled B in FIG. 8A.

FIG. 8C illustrates a wetting placed on the gel precursor layer of FIG. 8B.

FIG. 8D illustrates one or more inks added to the gel precursor layer of FIG. 8C. The one or more inks, the wetting solvent and the gelling agent at each sample location on the working electrode combine to form a gel at that sample location.

FIG. 8E illustrates each of the gels of FIG. 8D converted to a solid layer at each of the sample locations.

FIG. 8F illustrates the precursor assembly of FIG. 8E treated so as to generate a working electrode assembly having the desired sample compositions.

FIG. 9A is a topview of a wetting solvent placed on the gel precursor layer at the location that is desired for the sample layer.

FIG. 9B illustrates one or more inks added to the gel precursor layer of FIG. 9A. The one or more inks, the wetting solvent and the gelling agent at each sample location on the working electrode combine to form a gel.

FIG. 9C illustrates the gel of FIG. 9B converted to a solid layer at location desired for the sample layer.

FIG. 9D illustrates the precursor assembly of FIG. 9C treated so as to generate a working electrode assembly having the desired sample layer.

DESCRIPTION

Figure 1A:
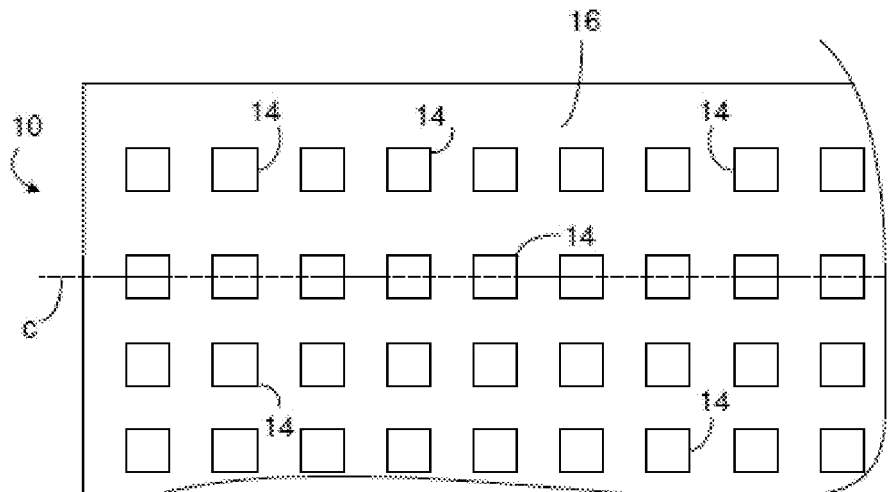
FIG. 1A through FIG. 1C illustrate an instrument for analyzing a material library.

As used herein and in the appended claims, the singular forms "a," "an," and "the" include plural referents unless the context clearly dictates otherwise. Thus, for example, reference to "a device" includes a plurality of such devices and reference to "the absorber" includes reference to one or more absorbers, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

The publications discussed above and throughout the text are provided solely for their disclosure prior to the filing date of the present application. Nothing herein is to be construed as an admission that the inventors are not entitled to antedate such disclosure by virtue of prior disclosure. Moreover, with respect to any term that is presented in one or more publications that is similar to, or identical with, a term that has been expressly defined in this disclosure, the definition of the term as expressly provided in this disclosure will control in all respects.

An instrument for screening a large number of analytes includes a library of samples located between a working electrode and a counter electrode assembly. The instrument allows measurement of one or more parameter that are each a function of a photocurrent through each sample in response to illumination of the sample by a light beam. The inventors have surprisingly found that parasitic reactions affect accurate measurements of these parameters. The effect of these parasitic currents on the quality of the results is a function of the separation between the working electrode and the counter electrode assembly. The instrument can be constructed such that the separation between the working electrode and the counter electrode assembly reduces the effects of these parasitic reactions. Additionally, the instrument can include electronics that correct for the presence of the parasitic reactions.

The inventors have also surprisingly found that the instrument has a dark current that fluctuates over time. Dark current refers to the instrument measuring a level of photocurrent for a sample even when the sample is not illuminated. The instrument can be configured to reduce the presence of dark current and can include electronics that correct for the presence of dark current.

The instrument includes an electrolyte between the working electrode and the counter electrode assembly. The electrolyte can be in contact with the samples and the counter electrode assembly. The electrolyte includes a redox couple. The redox couple is selected such that electrochemical oxidation and reduction can proceed without addition of a catalyst in the electrolyte or on the samples. The redox couple in contact with a sample or analyte may behave similar to an ideal metal contact. As such, identified pairings of redox couple and analyte aids the identification of metals for creating high quality contacts to the same analyte.

The samples can be generated from one or more gels formed on the working electrode. Alternately, the samples can be generated using physical vapor deposition (PVD) techniques such as sputter deposition. These methods permit formation of samples with a large range of compositions. Further, in contrast with prior methods for producing large numbers of samples on an electrode, these methods produce samples that are continuous across a suitably large area, have a substantially uniform thickness, and substantially uniform distribution of the analytes within the samples.

Figure 1B:
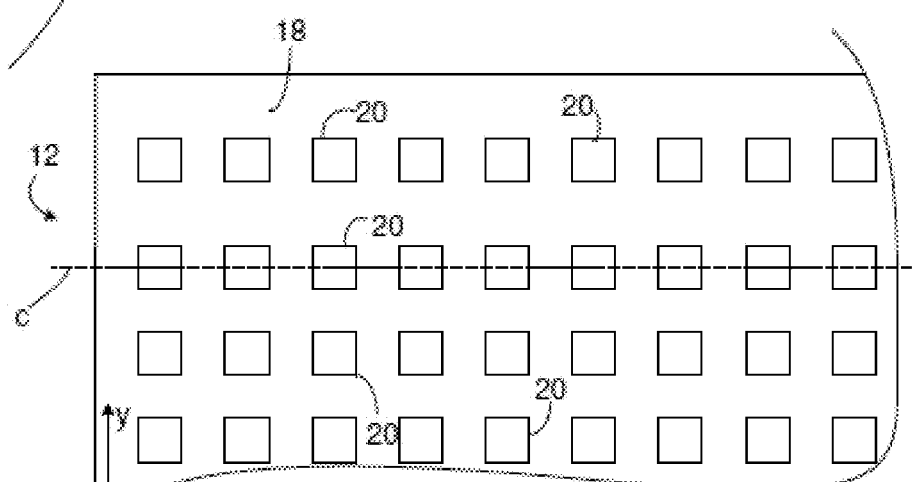
Figure 1C:
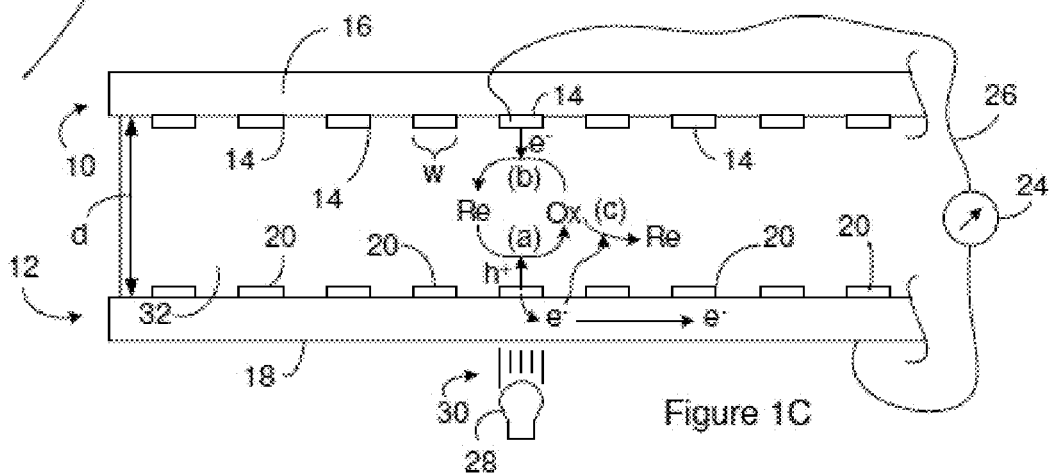

FIG. 1A through FIG. 1C illustrate an instrument for screening a material library for light absorption characteristics. FIG. 1A is a bottom view of a portion of a counter electrode assembly 10. FIG. 1B is a topview of a portion of a working electrode assembly 12. FIG. 1C illustrates an instrument that includes the counter electrode assembly 10 of FIG. 1A and the counter electrode assembly 10 of FIG. 1B. The portion of the counter electrode assembly show in FIG. 1C is a cross section of the counter electrode assembly 10 shown in FIG. 1A taken along the line labeled C in FIG. 1A. The portion of the working electrode assembly 12 show in FIG. 1C is a cross section of the working electrode assembly 12 shown in FIG. 1B taken along the line labeled C in FIG. 1B.

The counter electrode assembly 10 includes one or more counter electrodes 14 on a substrate 16. The instrument illustrated in FIG. 1A through FIG. 1C includes multiple counter electrodes 14 on a substrate 16. When the electrode assembly includes multiple counter electrodes 14, the counter electrode assembly 10 includes electrical connections that allow each of the counter electrodes 14 on the substrate 16 to be individually addressed by electronics (not shown) in electrical communication with the instrument. As a result, the counter electrode assembly 10 includes electrical connections that are not illustrated. The electrical connections can be in the form of metal traces on or through the substrate 16 as is know in the fabrication of integrated circuits.

The working electrode assembly 12 includes a working electrode 18. In some instances, the working electrode 18 is parallel or substantially parallel to the counter electrode assembly 10. A material library is arranged on or over the working electrode 18. The material library can include one or more continuous sample layers but is illustrated as including multiple samples 20 that each includes, consists essentially of, or consists of an analyte being screened by the instrument. The number of samples 20 included in a working electrode assembly 12 can exceed 100, 1000, or 5000. Accordingly, the instrument is suitable for quickly analyzing thousands of samples 20.

Figure 2A:
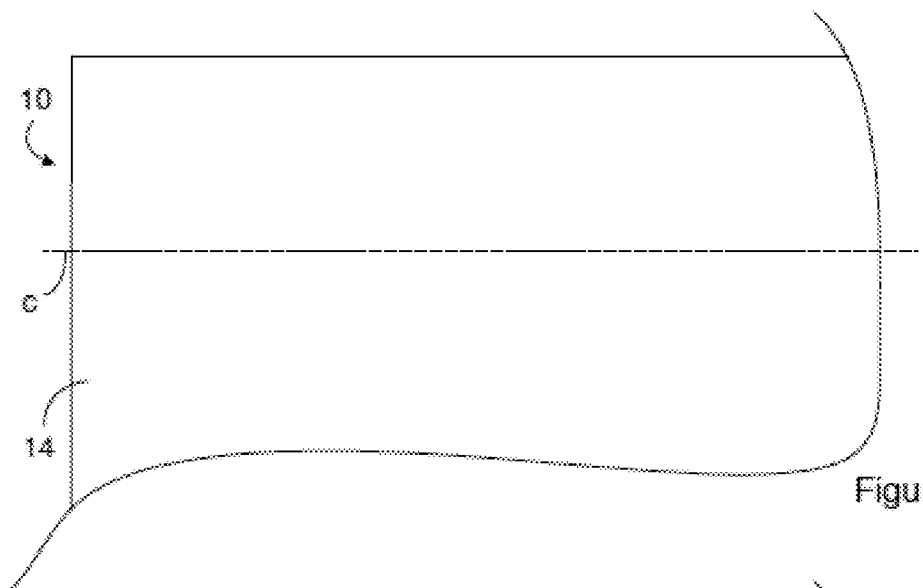
FIG. 2A through FIG. 2C illustrate the instrument of FIG. 1A through 1C with a single counter electrode associated with all of the samples on a working electrode.
Figure 2B:
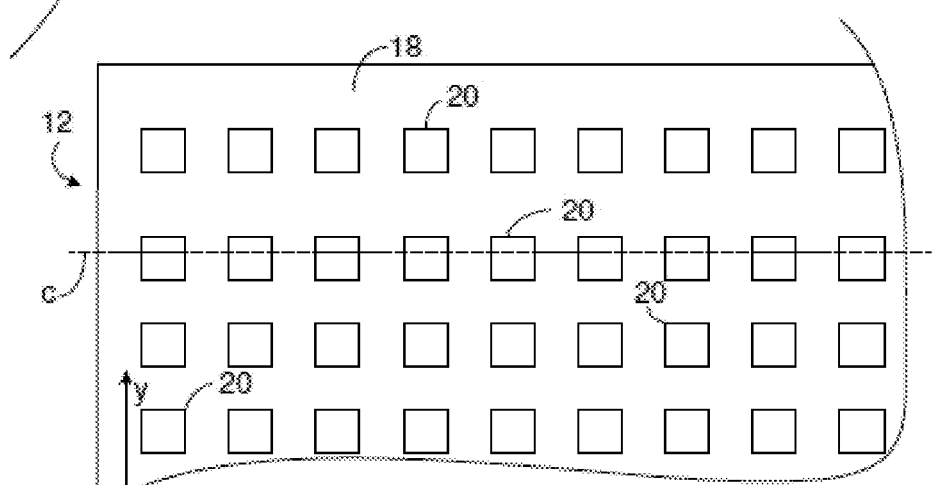
Figure 2C:
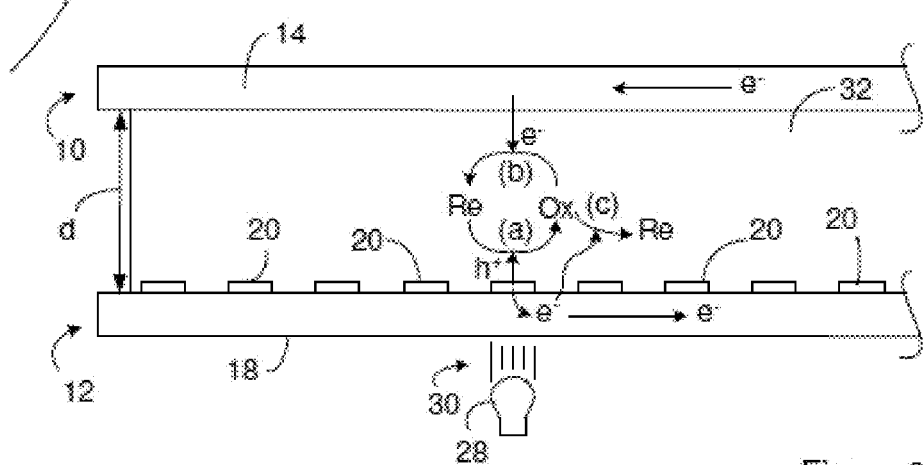

In FIG. 1C, each of the counter electrodes 14 is associated with a sample 20 in that the counter electrode 14 is directly above the associated sample 20. For instance, a line can be drawn that is perpendicular to the upper surface of the sample 20 or the upper surface of the portion of the working electrode 18 under the sample 20 such that the line passes through the associated counter electrode 14. However, a counter electrode 14 can be associated with multiple samples 20. For instance, FIG. 2A through FIG. 2C illustrate the instrument of FIG. 1A through 1C but with a single counter electrode 14 that is associated with each of the samples 20. FIG. 2A is a bottom view of a portion of the counter electrode assembly 10. FIG. 2B is a topview of a portion of a working electrode assembly 12. FIG. 2C illustrates an instrument that includes the counter electrode assembly 10 of FIG. 2A and the counter electrode assembly 10 of FIG. 2B. The portion of the counter electrode assembly 10 shown in FIG. 2C is a cross section of the counter electrode assembly 10 shown in FIG. 2A taken along the line labeled C in FIG. 2A. The portion of the working electrode assembly 12 show in FIG. 2C is a cross section of the working electrode assembly 12 shown in FIG. 2B taken along the line labeled C in FIG. 2B. The counter electrode assembly 10 includes a single counter electrode 14 that is associated with each of the samples 20.

Figure 3A:
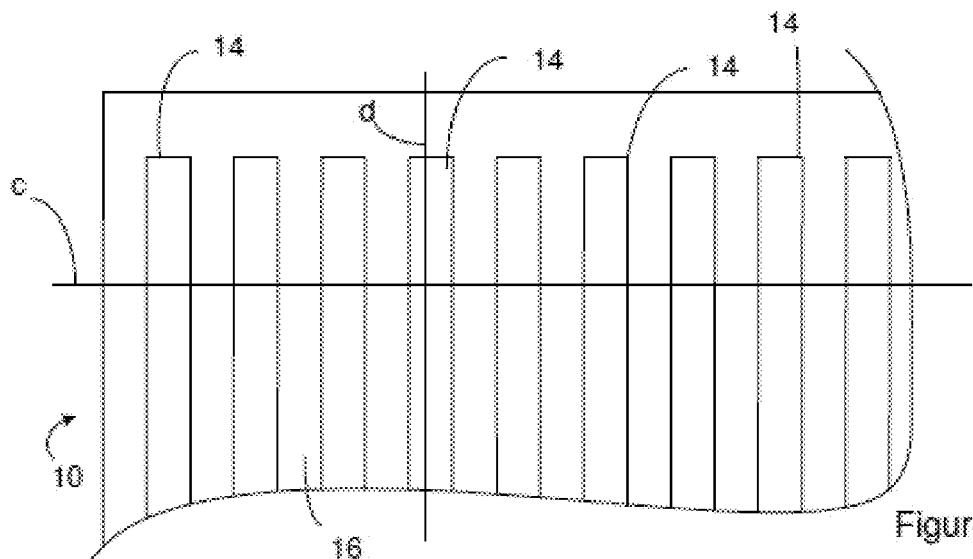
FIG. 3A through FIG. 3D illustrate the instrument of FIG. 1A through 1C but with multiple counter electrodes that are each associated with multiple samples on a working electrode.
Figure 3B:
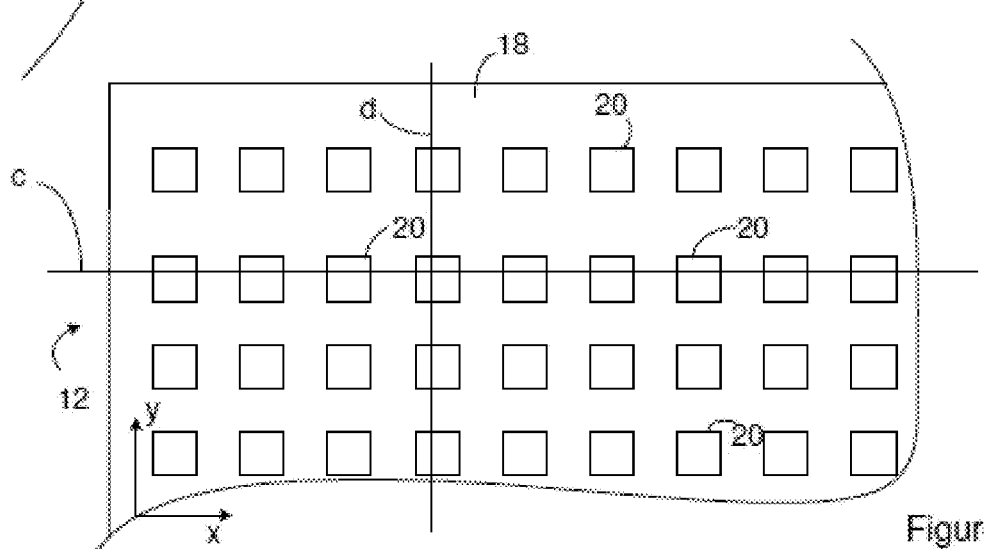
Figure 3C:
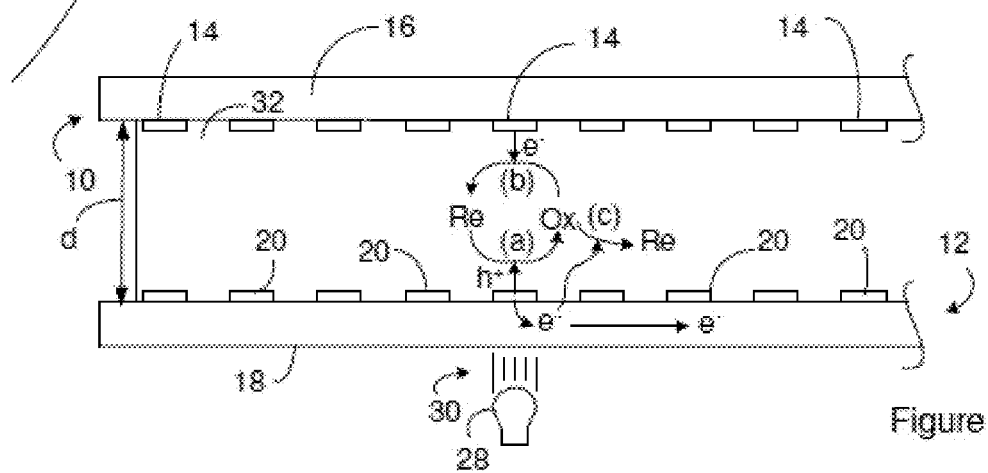
Figure 3D:
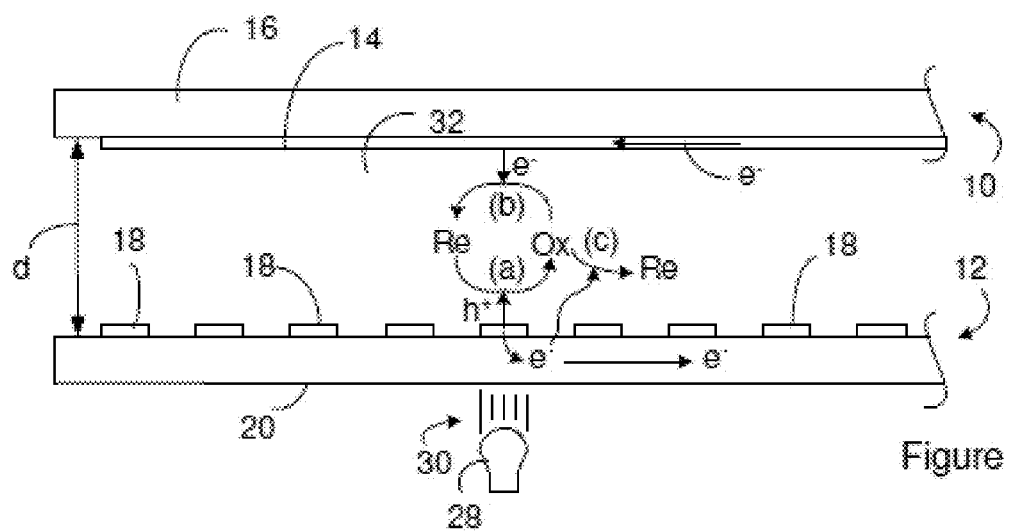

The counter electrode assembly 10 can also include multiple counter electrodes 14 that are each associated with more than one of the samples 20. For instance, FIG. 3A through FIG. 3D illustrate the instrument of FIG. 1A through 1C but with multiple counter electrodes 14 that are each associated with multiple samples 20. FIG. 3A is a bottom view of a portion of the counter electrode assembly 10. FIG. 3B is a topview of a portion of a working electrode assembly 12. FIG. 3C and FIG. 3D each illustrates an instrument that includes the counter electrode assembly 10 of FIG. 3A and the counter electrode assembly 10 of FIG. 3B. The portion of the counter electrode assembly 10 shown in FIG. 3C is a cross section of the counter electrode assembly 10 shown in FIG. 3A taken along the line labeled C in FIG. 3A. The portion of the working electrode assembly 12 show in FIG. 3C is a cross section of the working electrode assembly 12 shown in FIG. 3B taken along the line labeled C in FIG. 3B. Similarly, the portion of the counter electrode assembly 10 shown in FIG. 3D is a cross section of the counter electrode assembly 10 shown in FIG. 3A taken along the line labeled D in FIG. 3A. The portion of the working electrode assembly 12 show in FIG. 3D is a cross section of the working electrode assembly 12 shown in FIG. 3B taken along the line labeled D in FIG. 3B.

All or a portion of the samples 20 shown in FIG. 1B, FIG. 2B, or FIG. 3B can include or consist of the same analyte or different samples 20 can have a different analyte. In some instances, each of the different samples 20 on a working electrode 18 includes or consists of a different analyte. When different samples 20 have a different analyte, the analytes can have different selections of elements. Alternately, when different samples 20 have a different analyte, the analytes can have the same selection of elements but with the elements in different molar ratios. For instance, the analytes in different samples 20 can each consist of iron, nickel, and oxygen but one of the sample 20 can have a molar ratio of iron to nickel:iron of 3:1 and a second sample 20 can have the molar ratio of nickel:iron of 1:3.

The working electrodes 18 illustrated in FIG. 1B, FIG. 2B, and FIG. 3B include axes labeled x and y. The analytes can be arranged such that the analytes have a gradient of one or more elements in the x direction and/or in the y direction. For instance, the samples 20 can be arranged such that the molar percentage of a particular element in the analyte changes in the x direction and/or in the y direction. When the molar percentage of the analyte that is one or more particular elements changes in the x direction and in the y direction, the one or more elements that change in the x direction can be different from the one or more elements that change in the y direction.

Figure 4A:
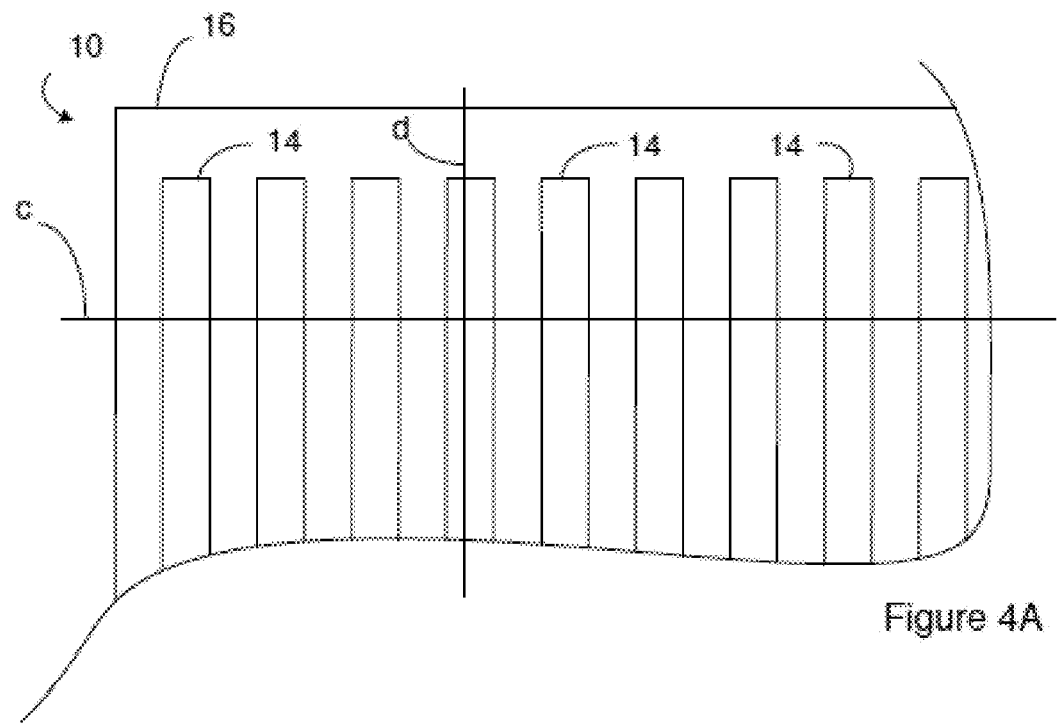
FIG. 4A through FIG. 4C illustrate the instrument of FIG. 3A through FIG. 3C modified so the samples illustrated in FIG. 3B are integrated into a continuous sample layer.
Figure 4B:
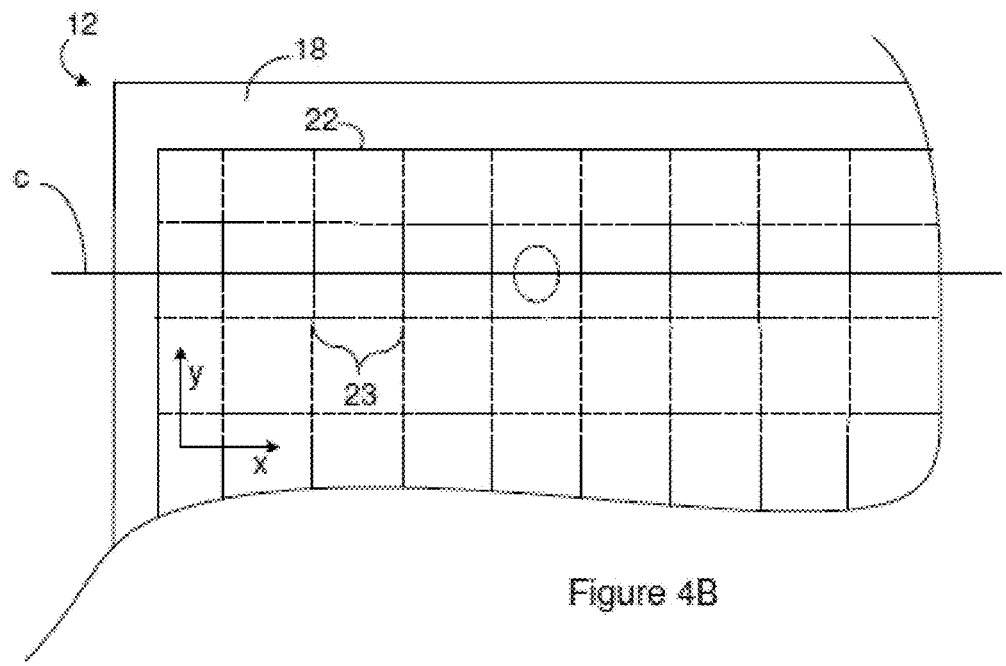
Figure 4C:
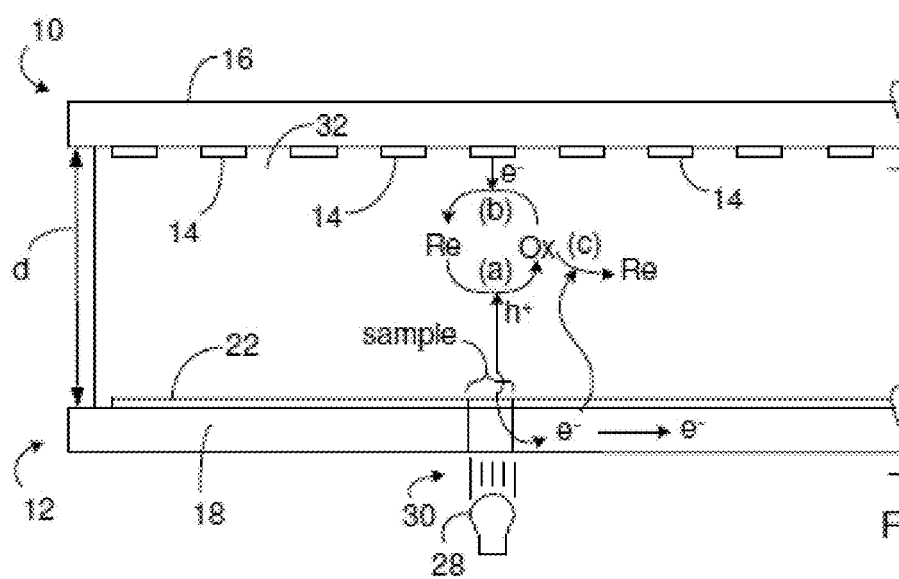

FIG. 1A through FIG. 3D illustrate the samples 20 on the working electrode 18 as being separated from one another. However, any of the instruments shown in FIG. 1A through FIG. 3D can integrate all or a portion of the samples 20 into a single sample layer 22. As an example, FIG. 4A through FIG. 4C illustrate the instrument of FIG. 3A through FIG. 3C modified so the samples 20 illustrated in FIG. 3B are integrated into a continuous sample layer 22. FIG. 4A is a bottom view of a portion of the counter electrode assembly 10. FIG. 4B is a topview of a portion of a working electrode assembly 12. FIG. 4C illustrates an instrument that includes the counter electrode assembly 10 of FIG. 4A and the counter electrode assembly 10 of FIG. 4B. The portion of the counter electrode assembly 10 shown in FIG. 4C is a cross section of the counter electrode assembly 10 shown in FIG. 4A taken along the line labeled C in FIG. 4A. The portion of the working electrode assembly 12 show in FIG. 4C is a cross section of the working electrode assembly 12 shown in FIG. 4B taken along the line labeled C in FIG. 4B.

The working electrode assembly 12 in FIG. 4B has a single sample layer 22 positioned on the working electrode 18; however, the working electrode 18 can include more than one sample layer 22. As will become evident from the below discussion, one or more of the sample layers 22 can include multiple samples 20 that each includes or consists of a different analyte.

An x-axis and a y-axis are labeled in FIG. 4B. The composition of a sample layer 22 can change in the x direction and/or in the y direction. For instance, one or more sample layers 22 on a working electrode 18 can include or consist of an analyte with a composition that changes in the x direction and/or in the y direction. As an example, a sample layer 22 can be arranged such that the molar percentage of the one or more elements in the analyte changes in the x direction and/or in the y direction. When the molar percentage of the analyte that is one or more particular elements changes in the x direction and in the y direction, the one or more elements that change in the x direction can be different from the one or more elements that change in the y direction. As an example, one of the sample layers 22 on the working electrode 18 can include iron, nickel and oxygen. The molar ratio of iron to nickel can change in the x direction while the molar ratio of iron to oxygen remains constant or substantially constant. In the y direction, the molar ratio of iron to oxygen can change while the molar ratio of iron to nickel remains constant or substantially constant.

The changing in composition of the analyte can be smooth and continuous across the sample layer. Alternately, the sample layer can optionally be divided into zones 23 as is illustrated by the dashed lines in FIG. 4B. Different zones can include different but the composition of analyte in a zone can be constant of substantially constant across the zone. In other words, there can optionally be no gradient or substantially no gradient in the composition of an analyte across a zone even though there is optionally a composition gradient across multiple zones. Accordingly, the working electrode can essentially be constructed as shown in FIG. 1B, FIG. 2B, and/or FIG. 3B but with each of the samples being continuous with the adjacent sample.

The location of a sample 20 within a sample layer 22 is determined by the location where a light beam 30 is incident on the sample layer 22. For instance, the dashed lines in FIG. 4B and FIG. 4C illustrate the location where a light beam 30 is incident upon the sample layer 22. The resulting sample 20 is labeled "sample" in FIG. 4C. Accordingly, the sample layer 22 can include many samples 20 and the samples 20 can overlap one another. In some instances, the samples are each selected to be within one of the zones 23 defined in the sample layer. As noted above, the counter electrodes are positioned over the samples that are associated with the counter electrode. Accordingly, the samples in the sample layer are preferably selected such that a line can be drawn that is perpendicular to an upper surface of the sample and that passes through one of the counter electrodes. In some instances, each sample defined in a sample layer is located between a light source and a counter electrode.

Although not illustrated, the instrument is in electrical communication with electronics that operate the instrument. The electronics are structured so as to selectively provide electrical communication between any one of the counter electrodes 14 and the working electrode 18. For instance, the electronics can identify a particular one of the counter electrodes 14 and provide electrical communication between the identified counter electrode 14 and the working electrode 18 without providing electrical communication between the working electrode 18 and the other counter electrodes 14 that are not identified. In some instances, the electrical communication between the working electrode 18 and the identified counter electrode 14 is an electrical short, substantially an electrical short, or approximates an electrical short. As will be discussed below, in some instances, the electronics identify more than one of the counter electrodes 14 and provide electrical communication between the working electrode 18 and each of the identified counter electrodes 14.

The electronics include one or more electrical current measuring devices 24. Examples of suitable current measuring devices 24 include, but are not limited to, ammeters. The electronics can employ the one or more current measuring devices 24 to measure the level of electrical current through any one of the counter electrodes 14. For instance, when the electronics provide electrical communication between the working electrode 18 and one of the identified counter electrodes 14 the electronics can provide an electrical pathway 26 between the working electrode 18 and the identified counter electrode 14 with an ammeter positioned to measure the electrical current through the electrical path. For the purposes of illustration, FIG. 1A illustrates an electrical path between the working electrode 18 and the counter electrode 14 that is associated with an illuminated sample 20. An ammeter is positioned along the electrical pathway 26 so as to measure the electrical current through the electrical pathway 26. The electrical pathway 26 effectively or substantially shorts the working electrode 18 and the counter electrode 14. The resistance provided by the ammeter prevents the pathway 26 from being a true short although the illustrated circuit can approximate a short.

The instrument includes one or more light sources 28. The instrument shown in FIG. 1A through FIG. 4C includes a single light source 28. Each light source 28 can be the source of one or more light beams 30 that are each incident on one of the samples 20 during operation of the instrument. In some instances, the light beam 30 is configured to be incident on a sample 20 over an area that is less than 10 cm$^2$, 1 mm$^2$, or 1 µm$^2$. The instrument shown in FIG. 1A through FIG. 4C shows a light beam 30 passing through the working electrode 18 before being incident on one of the samples 20. Accordingly, the working electrode 18 is transparent or substantially transparent to wavelengths of interest in the light beam 30. Although not shown, the samples 20 can alternately be illuminated from above the working electrode 18. For instance, the substrate 16 of the counter electrode 14 can be transparent or substantially transparent to wavelengths of interest in the light beam 30 and the light beam 30 can pass through the substrate 16 of the counter electrode 14 before being incident on the sample 20.

The one or more light sources 28 and/or the working electrode 18 are configured such that the electronics can identify or more of the samples 20 and cause the identified samples 20 to be illuminated by one or more of the light beams 30 while the unidentified samples 20 are not illuminated. For instance, the light source 28 can be moved relative to the samples 20 and/or the samples 20 can be moved relative to the light source 28 such that the electronics can identify a particular one of the samples 20 and then illuminate that sample 20 with one or more of the light beams 30.

The light source 28 can be selected to have a selection of wavelengths that is suitable for the intended purpose of the analyte. For instance, when the analytes are to be used as the light absorber in a photovoltaic cell (solar cell), the solar cell will generally be exposed to sunlight. As a result, when studying analytes for photovoltaic cells, a suitable selection of wavelengths for the light source 28 includes, but is not limited to, light sources 28 providing light with wavelengths greater than 1600 nm, 800 nm, or 400 nm and/or less than 100 nm, 500 nm, or 1000 nm. Suitable light sources 28 include, but are not limited to, light emitting diodes, lasers, and broadband lamps, and suitable light beams 30 that carry light from the source 28 to the sample 20 include, but are not limited to, a focused beam, a collimated beam, and an optical fiber. In some instances, the electronics can vary the wavelength of light in a light source 28 using a light source such as multiple light emitting diodes, laser, or a monochromator.

Suitable materials for the counter electrode 14 include, but are not limited to, platinum, gold, and fluorine doped tin oxide (FTO). When the counter electrode 14 is to be transparent or substantially transparent to one or more light beams 30, suitable materials for the counter electrode 14 include, but are not limited to, patterned platinum, patterned gold, and fluorine doped tin oxide (FTO). Suitable materials for the working electrode 18 include, but are not limited to, fluorine doped tin oxide (FTO), carbon, and titanium. When the working electrode 18 is to be transparent or substantially transparent to one or more light beams 30, suitable materials for the working electrode 18 include, but are not limited to, patterned platinum, patterned gold, and fluorine doped tin oxide (FTO). Suitable materials for the substrate 16 include, but are not limited to, glass, silicon, and carbon. When the substrate 16 is to be transparent or substantially transparent to one or more light beams 30, suitable materials for the substrate 16 include, but are not limited to glass, quartz, and sapphire.

In the instruments of FIG. 1A through FIG. 4C, an electrolyte 32 is located between the counter electrode assembly 10 and the working electrode assembly 12. The electrolyte 32 can be in physical contact with the counter electrode assembly 10 and the working electrode assembly 12. The electrolyte 32 can be a solid or a liquid. In some instances, the electrolyte 32 includes or consists of an electrolyte 32 solution.

The electrolyte 32 includes one or more redox couples. A redox couple is a reductant (reductant) and the corresponding oxidant (oxidant) such as $[Fe(CN)_6]^{3-}/[Fe(CN)_6]^{4-}$. The redox couple can be present in the electrolyte before operation of the instrument. For instance, the redox couple can be present in the electrolyte when none of the samples is generating a photocurrent. In some instances, the redox couple is selected such that neither the electrolyte 32 nor the sample 20 need include a catalyst for the analyte to exhibit a photocurrent. For instance, the redox couple can have an exchange current density of at least 1 mA cm$^{-2}$ such that any or substantially any photovoltage generated by the analyte or sample will catalyze oxidation or reduction of the redox couple. As an example, the redox couple can have a well-defined Nernstian potential with exchange current density of at least 1 mA cm$^{-2}$ for typical counter electrode material such as platinum, gold and copper. In some instances, the redox couple has an exchange current density of at least 1 mA cm$^{-2}$, 10 mA cm$^{-2}$, or 100 mA cm$^{-2}$ for platinum, gold and copper. It is desirable for the redox reaction for the redox couple to be a facile reaction for all or nearly all of the possible analytes. However, the characteristics of each analyte may be unknown. As a result, the redox couple should have the current densities for a wide range of materials. The materials platinum, gold and copper are believed to be different enough to represent a broad range of electrical conductors. Accordingly, a redox couple that has an exchange current density of at least 1 mA cm$^{-2}$, 10 mA cm$^{-2}$, or 100 mA cm$^{-2}$ for platinum, gold and copper is believed to be effective for use with all or nearly all of the possible analytes.

In some instances, the redox couple has an exchange current density of at least 1 mA cm$^{-2}$, 10 mA cm$^{-2}$, or 100 mA cm$^{-2}$, for one or more of the counter electrodes and/or for one or more of the samples or for one or more of the analytes. In one example, the redox couple has an exchange current density of at least 1 mA/cm$^2$, 10 mA/cm$^2$, or 100 mA/cm$^2$ for one or more of the counter electrodes and/or an exchange current density of at least 1 mA/cm$^2$, 10 mA/cm$^2$, or 100 mA/cm$^2$ for one or more of the samples. In one example, the redox couple has an exchange current density of at least 1 mA/cm$^2$, 10 mA/cm$^2$, or 100 mA/cm$^2$ for one or more of the counter electrodes and an exchange current density of at least 1 mA/cm$^2$, 10 mA/cm$^2$, or 100 mA/cm$^2$ for one or more of the samples that are associated with each of the counter electrodes having the indicated level of exchange current density. In another example, the redox couple has an exchange current density of at least 1 mA/cm$^2$, 10 mA/cm$^2$, or 100 mA/cm$^2$ for one or more of the counter electrodes and/or an exchange current density of at least 1 mA/cm$^2$, 10 mA/cm$^2$, or 100 mA/cm$^2$ for one or more of the analytes. In one example, the redox couple has an exchange current density of at least 1 mA/cm$^2$, 10 mA/cm$^2$, or 100 mA/cm$^2$ for one or more of the counter electrodes and an exchange current density of at least 1 mA/cm$^2$, 10 mA/cm$^2$, or 100 mA/cm$^2$ for one or more of the analytes that are associated with each of the counter electrodes having the indicated level of exchange current density. The exchange current densities set out in the above examples can be in addition, or as an alternative to, the exchange current densities set out for platinum, gold and copper. Examples of suitable redox couples include, but are not limited to, cobaltocene/cobaltocenium, and ferrocene/ferrocenium. In addition to the one or more redox couples, the electrolyte 32 can include a solvent including, but not limited to, water, methanol, and acetonitrile, with at least one supporting electrolyte including, but not limited to, potassium chloride, sodium sulfate, and lithium perchlorate. A suitable concentration for the redox couple in the electrolyte 32 includes concentrations greater than 1 µM, 0.1 mM, or 10 mM.

During operation of the instruments illustrated in FIG. 1A through FIG. 4C, the electronics identify a test sample for testing. The test sample is the sample that includes or consists of the analyte that is currently being screened by the instrument. The electronics provide electrical communication between the working electrode and the counter electrode 14 that is associated with the test sample with an ammeter configured to measure the electrical current through the resulting electrical pathway 26. For instance, the electronics can effectively or substantially short-circuit the working electrode and the associated counter electrode 14 with an ammeter positioned along the electrical pathway 26 between the working electrode and the associated counter electrode 14 so as to measure the electrical current along the pathway 26.

The electronics also cause one of the light beams to be incident on the test sample. The incidence of the light beam upon the test sample causes photo-excitations, typically thought of as of hole and electron pairs. The holes are transported to the interface between the sample and the electrolyte where they take part in the reaction labeled (a) in FIG. 1C, FIG. 2C, FIG. 3C and FIG. 3D. In reaction (a), the holes react with a reductant labeled "Re" so as to form an oxidant labeled "Ox." The oxidant can react with electrons at the surface of the counter electrode that is associated with the sample in the reaction labeled (b) in FIG. 1C, FIG. 2C, FIG. 3C and FIG. 3D. In reaction (b), the electrons from the counter electrode react with the oxidant so as to form the reductant. The electrons excited in the sample are transported into the working electrode. A portion of the electrons travel from the working electrode to the interface between the working electrode and the electrolyte where they can take part in reaction (c). In reaction (c), the electrons from the working electrode react with the oxidant so as to form the reductant, where the source oxidant may be the product of reaction (a). A portion of the electrons transported from the sample into the working electrode exit from the working electrode without taking part in reaction (c). For instance, these electrons can travel to the associated counter electrode through the electrical pathway provided by the electronics and can serve as the source of electrons for reaction (b), where the source oxidant may be the product of reaction (a). As such, the products of reaction (a) are the reactants of reactions (b) and (c), and vice versa such that the rate of reaction (a) is the sum of the reaction rates of (b) and (c).

The reactions (a)-(c) discussed above assume that the analyte is a photoanode; however, an analyte can be photocathode in which case the electron flow from the photoexcitation is transported into the electrolyte and the holes are transported to the working electrode. In this scenario, the arrows in reactions (a), (b), and (c) are reversed and electrons pass from the counter electrode to the working electrode and react with the photoexcited hole at the interface of the sample and working electrode. Accordingly, the instrument is suitable for screening analytes that produce photoanodic or photocathodic current.

The electronics employ the current measuring device 24 to measure the electrical current through the counter electrode associated with the test sample. The measured level of electrical current serves as the value of a rate parameter that indicates the rate of reaction (b); however, the rate of reaction (b) does not necessarily indicate the level of photocurrent from the analyte because a portion of the excited electrons are consumed by parasitic reaction (c). Because researchers are often interested in the level of photocurrent from the analyte, the rate of reaction (a) can be of more interest than the rate of reaction (b).

Figure 5:
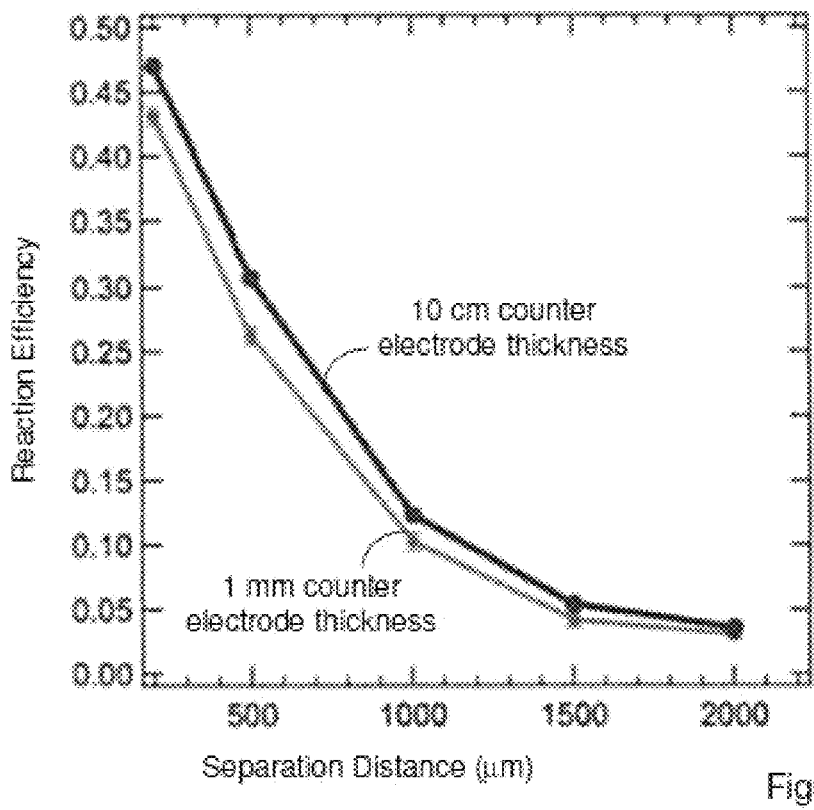
FIG. 5 shows the efficiency of a reaction as a function of the separation between a working electrode and a counter electrode assembly.

The reaction efficiency for the instrument can be expressed as the percentage of the photocurrent that is actually generated by the sample that is measured. Accordingly, the reaction efficiency is a ratio of the rate of reaction (b)/(rate of reaction (b)+rate of reaction (c)). A charge balance of the reactions shown in FIG. 1C, FIG. 2C, and FIG. 3C shows that the rate of reaction (a)=(rate of reaction (b)+rate of reaction (c). As a result, the reaction efficiency can also be written as the rate of reaction (b)/rate of reaction (a). The reaction efficiency is largely a function of the separation distance and the width of the counter electrode associated with the test sample. The width of a counter electrode is labeled w in FIG. 1C, FIG. 2C, FIG. 3C. The separation distance is the distance between the working electrode assembly and the counter electrode assembly and is labeled "d" in FIG. 1C, FIG. 2C, FIG. 3C and FIG. 3D. The reaction efficiency for the instrument has been numerically simulated and the results are presented in FIG. 5. FIG. 5 shows the reaction efficiency as a function of the separation distance. FIG. 5 illustrates that the instrument becomes more efficient as the working electrode assembly and counter electrode assembly approach one another. FIG. 5 also shows that the level of efficiency is a weak function of the counter electrode width. The separation distance for the instrument can be selected such that the reaction efficiency is greater than 0.01, 0.05, or 0.2. Accordingly, in some instances, the instrument has a separation distance less than 5, 1, or 0.5 mm in order for the instrument to operate at a suitable level of efficiency.

The results of FIG. 5 can be used to determine the rate of reaction (a). Since reaction efficiency is the rate of reaction (b)/rate of reaction (a), the electronics can determine the rate of reaction (a) from the rate of reaction (b)/the reaction efficiency. For instance, when the separation distance is around 1.5 mm, the reaction efficiency is about 5%. Additionally, suppose an ammeter measures the current due to reaction (b) at $R_b$ (Amp). In this instance, the electronics can determine the rate of reaction (a) as $R_b$ (Amp)/0.05.

Figure 6:
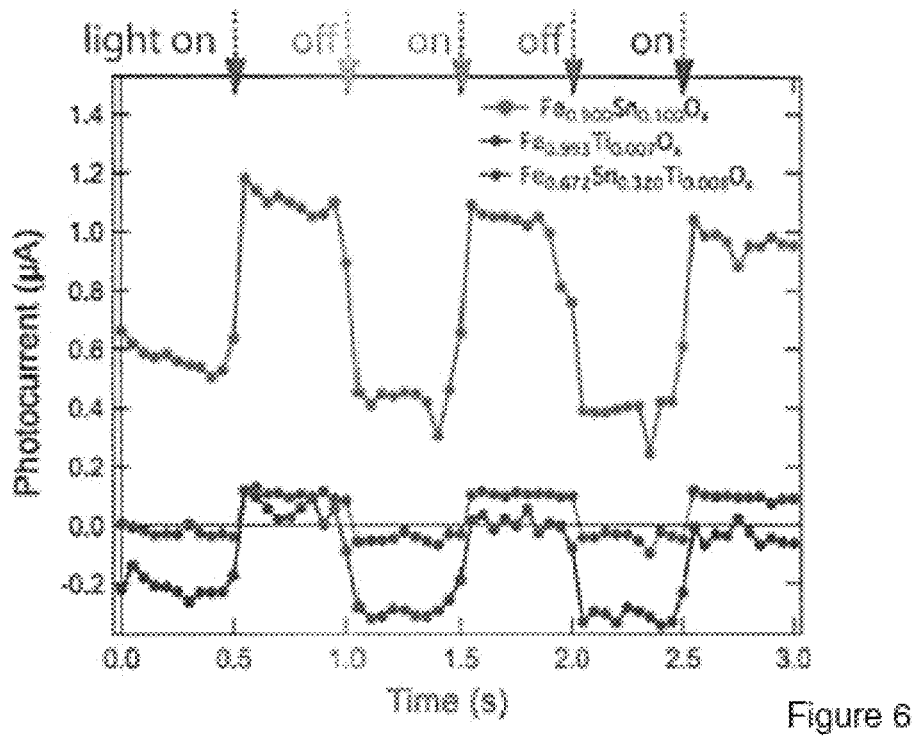
FIG. 6 presents experimental results showing measurement of photocurrent with different levels of dark current.

In some instances, the measured level of electrical current while the sample is illuminated can serve as an accurate indication for the rate of reaction (b). However, experimental results show that it may be necessary to correct for the effects of dark current. FIG. 6 shows experimental results for three different samples taken at different times using the same electrolyte, the same separation distance, and the counter electrode assembly, and the same light source. During the experiments, the light source was turned off and on so as to alternately illuminate the sample and then leave the sample dark. The electrical current measured by the ammeter (the rate of reaction (b)) versus time is shown in FIG. 6. FIG. 6 illustrates that there is still electrical current present when the samples were not illuminated by a light source. The electrical current that results when a sample is not illuminated is the dark current. The different samples shown in FIG. 6 each shows a different level of dark current. However, the effective difference in each set of data shown in FIG. 6 is that the data was taken at different times. As a result, FIG. 6 shows that the level of dark current in the instrument fluctuates with time. As a result, the electronics can optionally be configured to correct the current measurements from the ammeter for the effects of the fluctuating dark current.

It is believed that the dark current would average to zero if measured over a sufficiently long period of time. As a result, the electronics can employ different methods to generate an accurate measure of the electrical current through a counter electrode associated with a test sample. For instance, when a test sample is illuminated the electronics can average the electrical current measured through the associated counter electrode for at least the period of time that is sufficient for the dark current to be averaged out of the result. In these instances, the electronics use and/or report the averaged result as the final electrical current measurement. Alternately, the electronics can use a current differential. For instance, the electronics can measure current with the test sample illuminated by a light beam alternated with measuring current with the test sample not illuminated by the light beam. The current measurements with the test sample illuminated can include one or more individual current measurements and/or the current measurements with the test sample dark can include one or more individual current measurements. The electronics can generate a current differential by calculating the (current measured with the sample illuminated-current measured while dark). In some instances, the electronics average one, two, or three parameters to generate an average current differential where the one or more parameters are selected from a group consisting of the current differential, the current measured with the sample illuminated, and/or the current measured with the sample dark. Averaging over multiple illumination cycles can also be attained using electronics that incorporate a lock-in amplifier. The electronics can use the current differential or the averaged current differential as the final electrical current measurement. The use of the current differential in generating the final electrical current measurement may be desirable as it permits generation of the final electrical current measurement in a short time period. For instance, the date presented in FIG. 6 was generated in only a 3 second time-span.

Since the electronics can correct the measured electrical current for the effects of dark current, the electronics can generate an accurate approximation for the rate of reaction (b). The electronics can use the final electrical current measurement in combination with the data from FIG. 5 as described above in order to approximate the rate of reaction (a). The rate of reaction (a) indicates the photocurrent from the test sample or analyte provided in response to the illumination of the test sample. The rate of photon absorption and ensuing rate of charge transfer to the electrolyte solution is manifested as the rate of reaction (a). Further, the rate at which photons are incident on the test sample can also be determined by the electronics or provided to the electronics through an interface device such as keyboard. The electronics can divide the rate of reaction (a) by the rate at which photons are incident on the test sample to approximate the photon to current conversion efficiency.

Although FIG. 5 indicates that the reaction efficiency is not a strong function of the width of the counter electrode, experimental results have shown that the level of dark current increases as the width of the counter electrode increases. Accordingly, in some instances, one counter electrode, more that one of the counter electrodes, or all of the counter electrodes have a width less than 10 mm, 1 mm, or less than the width of the light beam in order to reduce the level of dark current.

One of the most difficult challenges in assembling structures using semiconductor light absorbers is making quality electrical contacts between the semiconductor and a metal electrical contact. Semiconductor/liquid contacts that use a redox couple with a well-defined redox potential provide an alternative to solid state contacts and offer a possibility for fast screening for suitable electrical contacts. The liquid contacts are often non-invasive and exhibit minimal interfacial reactions at the junction that could have compounding effects in probing the intrinsic properties of the semiconductor. Additionally, data developed as described above can be used to identify metals that can be used either as an ohmic contact or a rectifying contact to a particular analyte. For instance, when a high quality ohmic contact or rectifying junction is identified by a redox couple in contact with a sample or an analyte, a metal with the same electrochemical potential as the redox couple is generally suitable as the contact material for the semiconductor material. Alternately, when it is desirable to use a particular metal for a contact, a redox couple with a redox potential that matches the work function for the desired metal can be used in the electrolyte to screen for the analytes to be used in conjunction with the desired metal.

The above description describes measurement of parameters related to the photocurrent through a test sample and also the photon to current conversion efficiency for the test sample. However, the instrument can be used to generate this data for multiple samples in the library or for every sample in the library. For instance, the electronics can identify multiple test samples and then proceed from testing one test sample to another until each of the identified test samples has been screened.

In many instances, it is desirable merely to compare the results for different samples to one another. For instance, it may be desirable to identify the sample or group of samples that generate the largest photocurrent when illuminated by a particular light source. In these instances, it may not be necessary to use the reaction efficiency disclosed in the context of FIG. 5. For instance, when the data for different samples was generated using the same separation distance, the final measured electrical currents from different samples can be compared to one another without taking into account the reaction efficiency. In these instances, the sample with the largest rate for reaction (b) will generally have the largest rate of photon to current conversion. This result is possible because the process of correcting for the effects of separation distance is to multiply the rate for reaction (b) by a number that remains constant for a particular separation distance. As a result, when the data for different samples is generated using different separations distances, the reaction efficiency should be used before comparing the photocurrents generated by the different samples and/or before comparing the photon to current conversion efficiency of the different samples.

In some instances, the electronics test multiple samples at the same time. For instance, when the instrument includes multiple counter electrodes, the electronics can identify multiple test samples that are each associated with a different one of the counter electrodes, concurrently illuminate each of the test samples with one of the light beams, and concurrently provide electrical communication between the working electrode and each of the associated electrodes. As noted above, the electronics can include multiple currents measuring devices. The electronics arrange the current measuring devices such that each current measuring device indicates the amount of electrical current between the working electrode and one of the associated counter electrodes. The electronics can then concurrently test each of the test samples as described above. As a result, for each of the identified test samples the electronics can generate at least one or more parameters selected from a group consisting of a final electrical current measurement, absorption efficiency, level of photocurrent from the sample or analyte, and photon to current efficiency. Additionally, when the electronics can vary the wavelength of all or a portion of the one or more light sources, the electronics can generate the one or more of these parameters as a function of incident light wavelength by measuring the desired parameter at multiple different wavelengths.

Figure 7A:
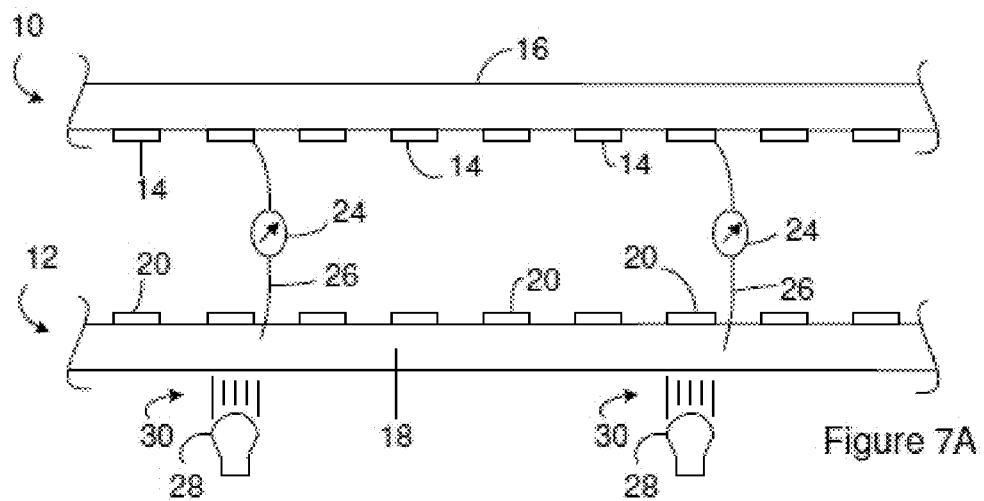
FIG. 7A illustrates adaptation of the instrument of FIG. 1C or FIG. 3C to concurrently test multiple samples on a working electrode.

FIG. 7A is provided to illustrate adaptation of the above instrument to concurrently test multiple samples 20. For the purposes of illustration, FIG. 7A illustrates adaptation of the instrument of FIG. 1C or FIG. 3C. The electronics identify two samples 20 as test samples and illuminate each of the test samples with a different light beam. An electrical pathway 26 is provided between the working electrode 18 and the counter electrode 14 associated with the test samples; however, there is not an electrical pathway provided from the working electrode 18 to the unidentified samples. Current measuring devices 24 such as ammeters are each arranged so as to measure the level of electrical current along one of the electrical pathways 26.

Figure 7B:
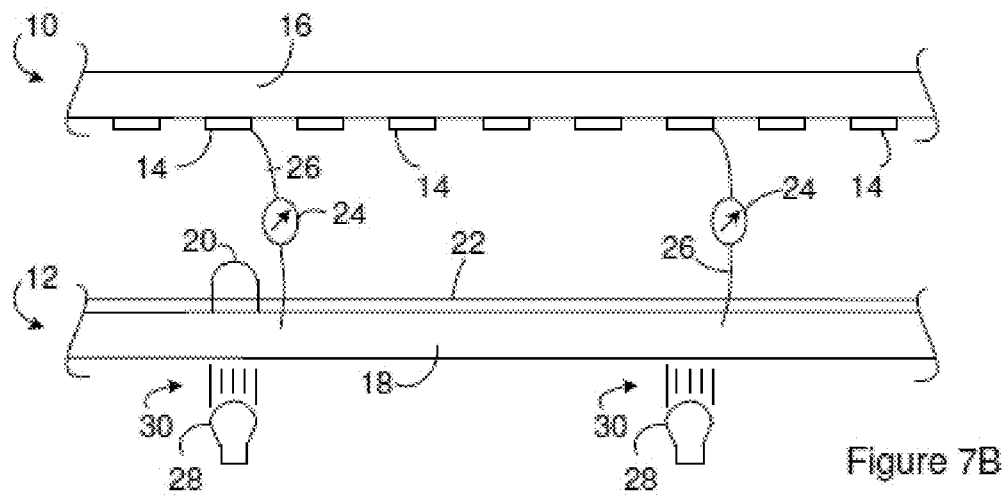
FIG. 7B illustrate adaptation of the instrument of FIG. 4C to concurrently test multiple samples on a working electrode.

FIG. 7B illustrate adaptation of the instrument of FIG. 4C to concurrently test multiple samples included in a sample layer. In FIG. 7B, two areas of the sample layer 22 that are identified as test samples and are each illuminated by a different light beam 30. An electrical pathway 26 is provided between the working electrode 18 and the counter electrode 14 associated with the test samples; however, there is not an electrical pathway provided from the working electrode 18 to the unidentified samples. Current measuring devices 24 such as ammeters are each arranged so as to measure the level of electrical current along one of the electrical pathways 26.

The primary concern when concurrently testing multiple samples is the cross talk between the associated counter electrodes. Experimental evidence has shown that, in some instances, when a first one of the associated counter electrodes is separated from a second one of the associated counter electrodes by more than 32 mm, the electrical current through the first counter electrodes as a result of the second counter electrode is less than 3% of the electrical current through the second counter electrode. For instance, this has been shown to be the case for at least instances when the separation distance (d) is 1 mm or on the order of 1 mm. Accordingly, in some instances where the electronics concurrently test multiple test samples, the test samples are separated by more than 10 mm, 30 mm, or 10 times the separation distance (d).

The above description describes identification and testing of a single set of test samples; however, the instrument can be used to sequentially screen multiple set of test samples until a targeted selection of samples have been tested or until all of the samples have been tested. For instance, the electronics can sequentially identify multiple sets of test samples and then proceed from testing one set of test samples to another set of test sample until each sample in the targeted selection of test samples has been tested.

Suitable analytes include, but are not limited to, light absorbers. When a photon of a particular wavelength is incident on a light absorber, the photon can excite a hole-electron pair within the light absorber. As a result, light absorbers can be suitable for use with a range of wavelengths. Since the light absorbers are often used in applications such as solar cells and solar fuel generators, it is often desirable for the light absorbers to absorb sunlight. Accordingly, in some instances, the analytes include light absorbers that absorb light at wavelengths greater than 1600 nm, 800 nm, or 400 nm and/or less than 100 nm, 500 nm, or 1000 nm; however, light absorbers that absorb light at other wavelengths are possible.

Examples of suitable light absorbers include, but are not limited to, semiconductors. Suitable semiconductors include elemental materials such as silicon which are native semiconductors, or compounds or materials that include one or more cations and one or more anions. Suitable cations include, but are not limited to, cations of metals and transition metals, Fe, Ti and Cd. Suitable anions include anions such as O, S, and Te. These anions are often sourced from reactive gases, which are each a gas at STP (standard temperature and pressure) and not a noble a gas. Examples of reactive gases include, but are not limited to, $O_2$, $N_2$, $NH_3$, $CH_4$, and $H_2S$. In one example, at least a portion or all of the analytes each includes one or more metal elements and includes one or more anions, and is selected from the group consisting of a binary material or compound, a ternary material or compound, and a quaternary material or compound. In some instances, at least a portion or all of the analytes each includes a binary oxide, a ternary oxide, a quaternary oxide, a ternary oxynitride, and a quaternary oxynitride. In some instances, at least a portion or all of the analytes each includes two or more metal elements and two or more anions.

One method for making the samples on the working electrode is to use ink jet printing to dispense a liquid drop onto a particular location on the working electrode. The drop includes one or more components for the desired analyte. The drop is then dried so as to provide a solid layer that includes at least a portion of the analyte components. In some instances, the solid layer is processed further in order to generate the desired analyte. In some instances, the liquid drop is formed on the working electrode by combining the liquid from several different inks jets. Depending on various interactions between the ink solutions and the working electrode, the intended drop of liquid can break into several smaller drops resulting in a sample that is not continuous over the desired area. When the sample is not continuous over an area with dimensions on the order of the incident wavelength, the results provided by the instrument can become unreliable or even useless. Further, the presence of smaller drops may prevent different components from mixing and can accordingly prevent formation of the desired analyte. Additionally, the effects of surface tension cause the thickness of the liquid drop to vary across the surface of the working electrode. Variations in the thickness of the liquid drop translate into variations in the thickness of the resulting analyte and/or sample. Variations in the thickness of the sample and/or analyte can reduce the quality of results provided by the instrument. As a result, it is desirable for the sample and/or analyte to have a constant or substantially constant thickness.

The use of a gel as a precursor for the sample can provide the samples with continuity over the desired area and also with consistency in the thickness of the sample over the area and even distribution of the one or more analytes within the sample. A gel is recognized as a different phase of matter than liquids and solids. Many gels are composed primarily of a liquid with a cross-linked gelling agent.

When forming a working electrode having discrete samples as shown in FIG. 1A through FIG. 3D, a gel can be formed at one, more than one, or all of the locations on the working electrode where the samples are desired. Each gel can include one or more components for the analyte that is to be positioned at that location, a gelling agent, and one or more solvents such as wetting solvents and ink solvents (carrier liquid). The one or more components can be all of the components of the desired analyte or only a portion of the components for the desired analyte. The use of the gel reduces the tendency of the samples to split into non-contiguous regions. Further, components for the analyte can diffuse through the gel allowing mixing of the different components even though the components are added to the gel at different times and/or different locations in the gel.

The gel can be used to generate a solid layer that includes or consists of the analyte components that were previously included in the gel. For instance, the gel can be converted to the solid by drying the gel such that the concentration of analyte components exceed their solubility limit in the carrier liquid and precipitate onto the substrate. Drying the gel can include removing the one or more solvents through methods such as evaporation. A gel dries from both the top and the sides. As a result, during drying, a two-phase system occurs where a solid layer is in contact with the remaining gel. The gels can be dried until a solid layer of material remains on the working electrode. The solid layer includes, consists of, or consists essentially of the one or more components for the analyte and the gelling agent. In contrast with liquids, during drying, convective currents do not form within the gel. When drying a liquid, these convective currents can carry components for the analyte to the surface of the liquid and create an uneven distribution of these components across the resulting sample. The lack of these currents within a drying gel and the ability of the components to diffuse throughout the gel allows the one or more components for the analyte to become evenly distributed throughout the solid layer that results from drying of the gel. Suitable methods for drying the gel include, but are not limited to, one or more techniques selected from a group consisting of long exposure to ambient conditions, application of reduced pressures to accelerate evaporation, and application of heat to accelerate evaporation. Other methods of using the gel to generate the solid layer include, but are not limited to, evaporation of the wetting solvent, application of light to induce photochemical reactions and addition of an agent to induce precipitation.

Another method for using the gel to generate the solid layer includes the use of electroplating. For instance, an electrical potential can be applied to the working electrode such that the solid layer is electroplated onto the working electrode. The use of electroplating also results in a two-phase system where the solid layer is in contact with the remaining gel. Since the electroplating does not necessarily result in the wetting solvents and/or any ink solvents being removed from the gel, the gel remains in contact with the solid layer after formation of the solid layer has been completed. Additionally, the solid layer includes the one or more components that are to be incorporated into the analyte but, in some instances, does not include the gelling agent. The gel that remains in the sample location after the formation of the solid layer can be removed by physical scraping, thermal treatments, or washing with additional solvents. In some instances, electroplating the solid layer onto the working electrode from the gel is preferred to precipitation of analyte components through drying the gel because the electroplating technique produces a more desirable assembly of the analyte components. Further, in some instances, electroplating directly produces the desired analyte(s) and thermal treatment is not needed or not performed.

In some instances, the one or more components for the analyte can include or consist of anions and/or cations that are included in the analyte; however, in some instances, the one or more components can include uncharged species. The anions, cations, and uncharged species can include or consist of one element or multiple elements. In some instances, the one or more components form a salt and the solid layer includes, consists essentially of, or consists of the salt and the gelling agent. In some instances, one or more of the analyte components includes or consists of one or more metals. In some instances, each of the analyte components included in the gel includes or consists of one or more metals. For instance, when the analytes are to include iron, nickel, and oxygen, the gel can include only two analyte components. One of those components can be iron cations and the other can be nickel cations.

The process of forming the gel can include the use of inkjet printing. Inkjet printing is a technology for applying inks to a substrate such as the working electrode. A gel can include one or more of the inks applied by inkjet printing. Each of the inks can include one or more of the components for the analyte dissolved or suspended in a one more ink solvents. For instance, if a sample is to include iron and nickel, one ink can include or consist of a molecule containing iron dissolved in an ink solvent and another ink can include or consist of a molecule containing nickel dissolved in an ink solvent. The inks are included in the gel in a ratio that provides a target ratio for these components. For instance, if a sample is to have a 1:1 molar ratios of iron and nickel, the inks are added to the gel at a ratio that result in the gel having a 1:1 molar ratio of iron and nickel. The ability to change the ratio at which different inks are added to different gels provides a simple method for making different gels with different component ratios.

The gel can be formed in a variety of different sequences. For instance, a solid or liquid gelling agent can first be placed on the working electrode. A wetting solvent can be added to the gelling agent. Inkjet printing can then be used to add the desired inks to the mixture. Alternately, inkjet printing can then be used to add the desired inks to the gelling agent followed by the addition of the wetting solvent. Before achieving the gel phase, the mixture can be a two-phase system that includes both gel and solid or both gel and liquid. The mixture will generally become a single-phase gel after the level of solvents (ink solvents and wetting solvent) has risen above a threshold level. Accordingly, the gel phase can be achieved during or after the addition of the wetting solvent. Alternately, the gel phase can be achieved during or after the addition of the inks. The wetting solvent is optional. For instance, the inks solvents may be sufficient to form the single-phase gel when the mixed with the ink solvents. Accordingly, the above methods for forming the gel may be performed without the use of a wetting solvent. As noted above, the analyte components can diffuse through a gel. Accordingly, the inks can be added concurrently or sequentially and/or the inks can be added to the mixture in the same location or at different locations.

The various parts of the gel can be added in different sequences than are disclosed above. For instance, the inks and/or wetting solvent can be placed on the working electrode before the gelling agent. Additionally or alternately, inks can be mixed together before being printed on the working electrode. Further, the various constituents of the gel can be located in source other than the disclosed source. For instance, one or more components of the analyte can be mixed with the gelling agent before the gelling agent is applied to the working electrode. Alternately, the gelling agent can be included in one or more of the inks at a level where the ink is still in a liquid phase that allows the inkjet to be applied by through an inkjet.

Suitable gelling agents include, but are not limited to, agarose, Pluronic F-127, Pluronic P-123 polymers that act as gelling agents including cross-linked polymeric gelling agents. A particular example of a suitable gelling agent is agarose. Suitable wetting solvents include, but are not limited to, water, water containing 5-50% diethylene glycol, and water containing 5-50% ethanol. Suitable ink solvents include, but are not limited to, water, water containing 5-50% diethylene glycol, water containing 5-50% diethylene glycol and 0.5-5% diethylene glycol monobutyl ether, water containing nitric and/or hydrochloric acid, water containing 5-50% ethanol and other liquids commonly called "carrier liquids" in ink jet printing technologies. When a wetting solvent is used to generate a gel, the wetting solvent can be the same or different from one or more of the ink solvents.

Drying the gel results in a solid layer that includes the one or more components for the analyte and the gelling agent. The solid layer can be thermally treated in order to generate the desired analyte. When there is gelling agent present in the solid layer, the gelling agent can be selected such that the thermal treatment removes the gelling agent from the solid layer. Additionally, the thermal treatment can be performed so as to provide a phase change such as a transition from an amorphous material to a crystalline material or to change from one crystal phase to another crystal phase. Examples of suitable thermal treatments include, but are not limited to, pyrolysis, calcination, annealing, and sintering. The thermal treatment can be performed so as to add one or more additional components to the analyte. For instance, the thermal treatment can be performed in an atmosphere that includes or consists of a reactive gas in order to add one or more elements from the reactive gas to the analyte. As an example, the thermal treatment can be performed in oxygen atmosphere to generate oxide analytes. As another example, the thermal treatment can be performed in an atmosphere that includes or consists of nitrogen or ammonia to generate nitride analytes. The thermal treatment can be performed in an atmosphere that includes or consists of oxygen and nitrogen to generate oxynitride analytes. As an example, when the analytes are to include iron, nickel, and oxygen, the gels can include only two analyte components. One of those components can be iron cations and the other can be nickel cations. The resulting solid layers will include the gelling agent and a salt that include the nickel and the iron. The solid layer can then be thermally treated in an oxygen atmosphere to generate an analyte that includes the nickel, iron and oxygen.

Figure 8E:
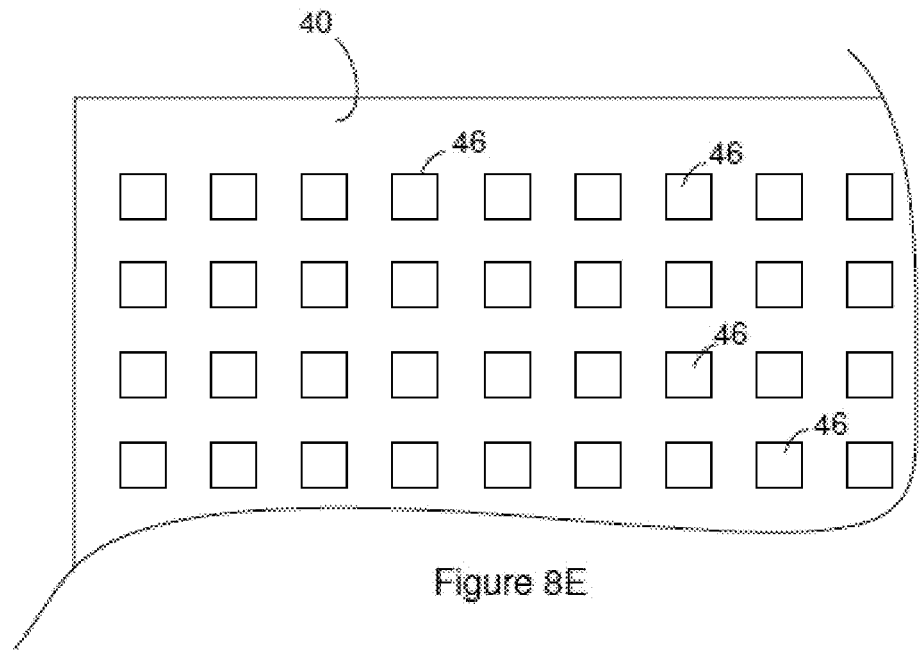
Figure 8F:
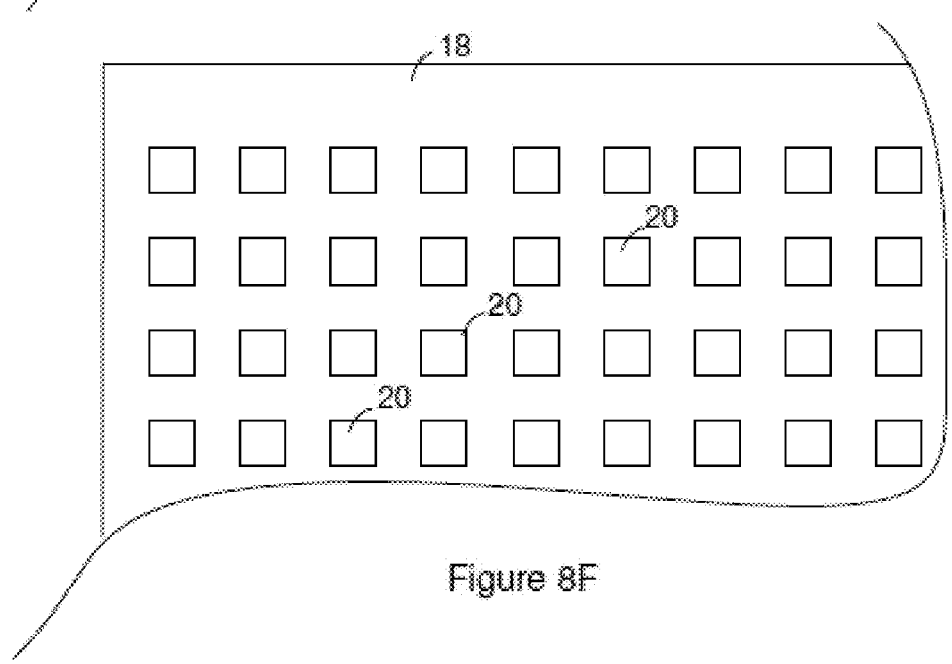

FIG. 8A through FIG. 8F illustrate a possible method for generating a working electrode assembly according to FIG. 1B, FIG. 2B, and FIG. 3B. A gel precursor layer 40 is formed on a working electrode so as to provide the assembly precursor of FIG. 8A and FIG. 8B. FIG. 8A is a topview of the assembly precursor and FIG. 8B is a cross section of the assembly precursor shown in FIG. 8A taken along the line labeled B in FIG. 8A. The gel precursor layer 40 is formed over the sample locations on the working electrodes as well as between the sample locations. The gel precursor layer 40 includes or consists of the gelling agent. Suitable methods of forming the gel precursor layer 40 on the working electrode include, but are not limited to, spin casting, dip coating, spraying and inkjet printing.

When a wetting solvent is used, the wetting solvent is placed on the gel precursor layer 40 so as to form primed gelling agent 42 at each of the sample locations so as to provide the assembly precursor of FIG. 8C. Alternatively the wetting solvent can be deposited during the deposition of one or more inks or after the deposition of the inks has completed. The portions of the gel precursor layer 40 that do not receive the wetting agent serve as a barrier between adjacent sample locations. Suitable methods for placing the wetting solvent on the gel precursor layer 40 include, but are not limited to, inkjet printing, pipetting, and application of solvent through a patterned gasket. Completed deposition of the wetting solvent and one or more inks provides the assembly precursor of FIG. 8D. The one or more inks, the wetting solvent and the gelling agent at each sample location combine to form a gel 44 at that sample location. The inks can be delivered to different sample locations in different ratios in order to generate different analytes at different sample locations. Suitable methods for adding the inks to a sample location include, but are not limited to, inkjet printing and pipetting.

The one or more inks that are to be delivered to a sample location can be concurrently or sequentially added to that sample location. When multiple inks are to be added to a sample location, the inks can be concurrently or sequentially added to the sample location. Inks added to the same sample location can be added to the same regions of the sample location. However, the wetting solvent provides a pathway through which the one or more analyte components in each of the one or more inks can diffuse and mix. As a result, different inks can optionally be added to a sample location at different regions of the sample location.

The gels can be converted to solids so as to provide a solid layer 46 at each of the sample locations as shown in the assembly precursor of FIG. 8E. For instance, the gel can be used to generate the solid layer through methods including, but not limited to, the techniques discussed above, drying, electroplating, evaporation of the wetting solvent, application of light to the gel to induce photochemical reactions and addition of an agent to the gel to induce precipitation. The assembly precursor of FIG. 8E can be thermally treated so as to provide the working electrode of FIG. 8F. The thermal treatment removes at least the gelling agent from between adjacent sample locations and can expose the underlying working electrode. As described above, the thermal treatment also removes the gelling agent from the solid layer 46 and can convert the material in each of the solid layers 46 to the desired form.

As noted above, the use of the wetting solvent is optional, accordingly, the method of FIG. 8A through FIG. 8F can be modified by adding the one or more inks for each sample location directly to the gel precursor layer 40 without adding the wetting solvent. The inks and the gelling precursor would then combine to form the gels at each of the sample locations. Accordingly, the method illustrated in FIG. 8A through FIG. 8F would proceed from the assembly precursor of FIG. 8A and FIG. 8B to the assembly precursor of FIG. 8D.

The above methods can also be applied to the generation of a continuous sample layers as disclosed in the context of FIG. 4B. For instance, a gradient of an analyte component can be created in the sample layer by varying the delivery of the ink that includes that component. For instance, in order to create a gradient of a target component that increases moving in an x direction on the working electrode, the amount of ink that includes the target component can be increased as the ink is delivered to locations that are further along the x direction on the working electrode.

FIG. 9A through FIG. 9D illustrate a method of forming a working electrode according to FIG. 4B. The method makes use of an assembly precursor constructed according to FIG. 8A and FIG. 8B. The gel precursor layer 40 is formed on the working electrode so as to cover at least the region of the working electrode where the sample layer is to be positioned.

Figure 9A:
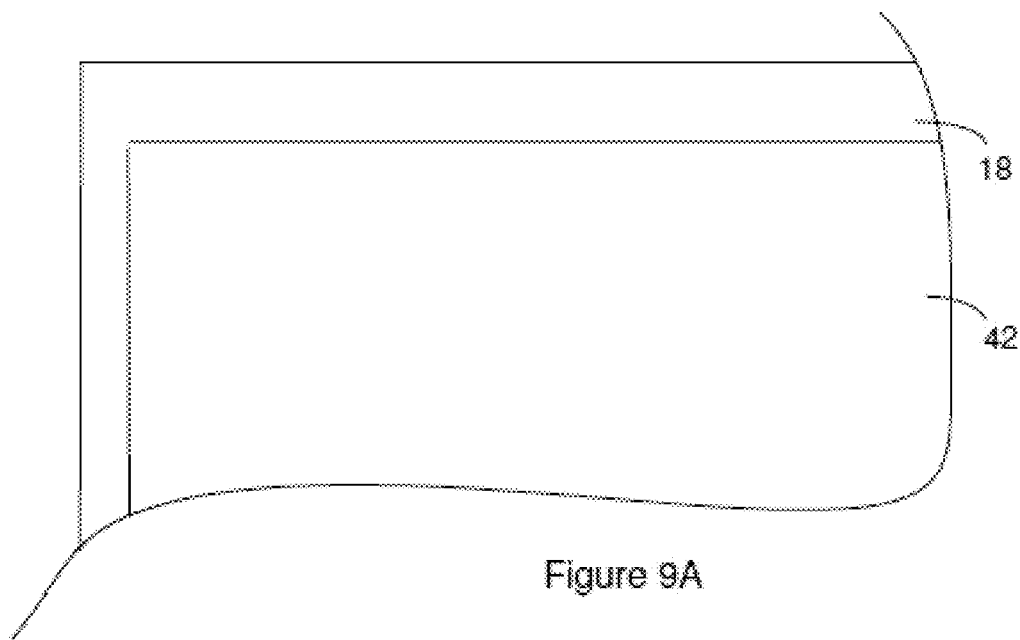
FIG. 9A through FIG. 9D illustrate a method of forming a sample layer on a working electrode according to FIG. 4B. The method makes use of an assembly precursor constructed according to FIG. 8A and FIG. 8B. The gel precursor layer is formed on the working electrode so as to cover at least the region of the working electrode where the sample layer is to be positioned.
Figure 9B:
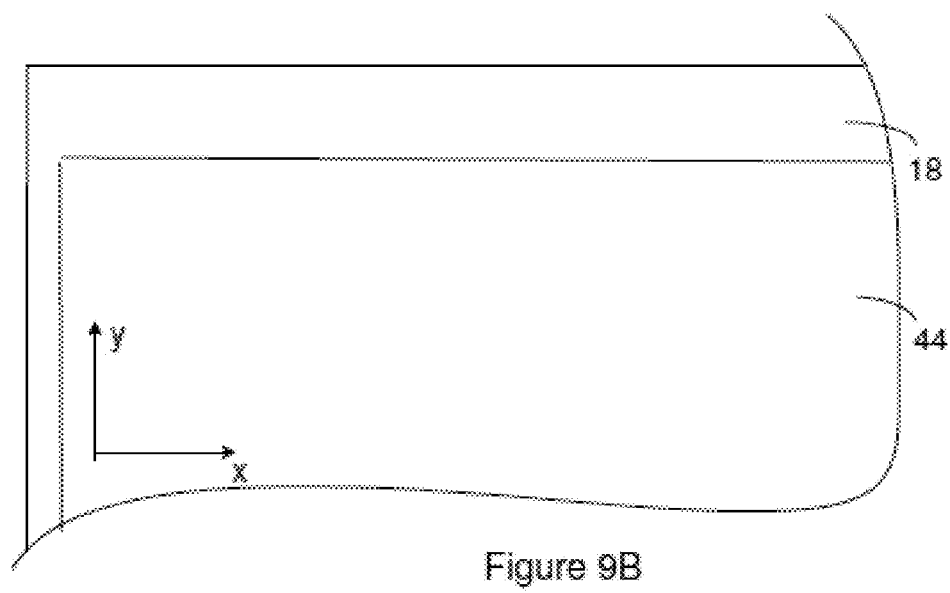

When a wetting solvent is used, the wetting solvent is placed on the gel precursor layer 40 so as to form a primed gel precursor at location that is desired for the sample layer as shown in FIG. 9A. After placement of the wetting solvent, the one or more inks can be added to wetting solvent so as to provide the assembly precursor of FIG. 9B. The one or more inks, the wetting solvent and the gelling agent at each sample location can combine to form a gel 44 in the location where the sample layer will be formed. The ratio of the amount of different inks that are delivered to different locations on the gel precursor layer 40 can be varied so as to achieve any desired gradients for the composition of the resulting analytes. The inks can be added so as to provide a smooth and continuous analyte composition gradient across all or a portion of the resulting sample layer. Alternately, the inks can be added to different zones of the sample layer as discussed in the context of FIG. 4B. For instance, the inks can be added so as to generate different analytes in different zones of the sample layer but such that the composition of analyte in a zone is constant or substantially constant across the zone. The one or more inks delivered to the gel precursor layer 40 can be delivered to the gel precursor layer 40 sequentially or concurrently. Suitable methods for adding the inks to a sample location include, but are not limited to, inkjet printing and pipetting.

Figure 9C:
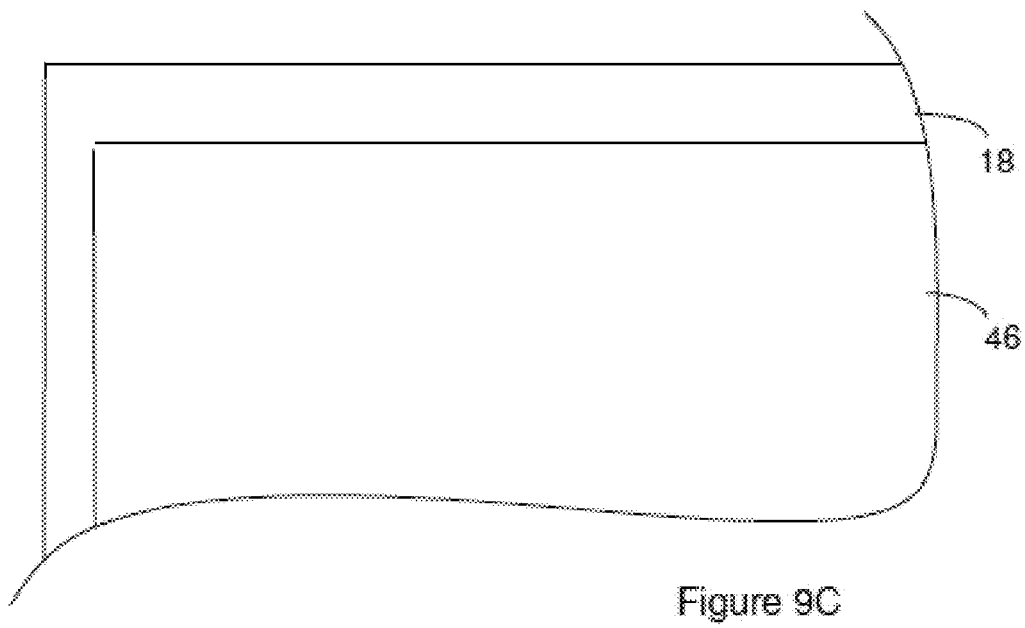
Figure 9D:
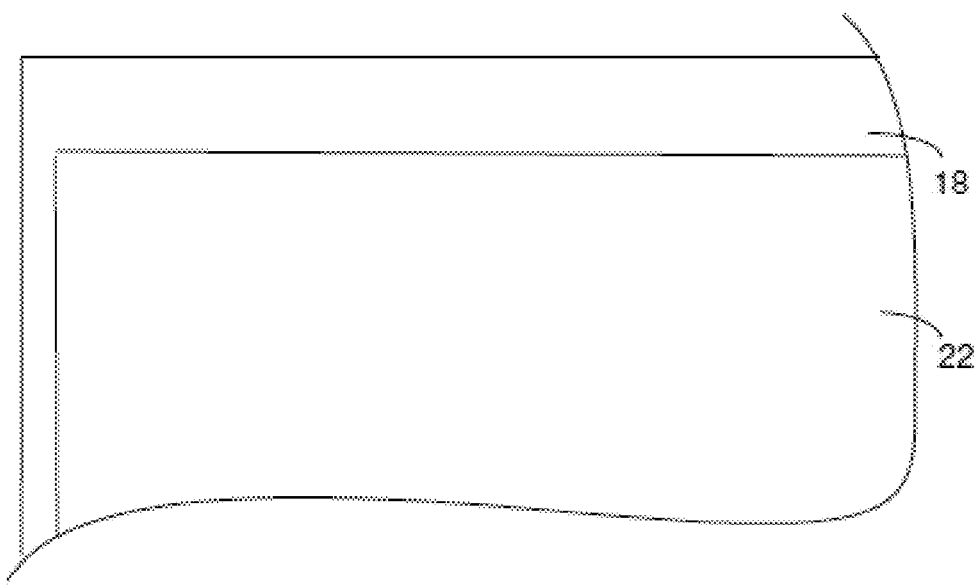

The gel 44 can be converted to solids so as to provide a solid layer 46 where the sample layer will be formed as shown in the assembly precursor of FIG. 9C. For instance, the gel can be used to generate the solid layer through methods including, but not limited to, the techniques discussed above, drying, electroplating, evaporation of the wetting solvent, application of light to the gel to induce photochemical reactions and addition of an agent to the gel to induce precipitation. The assembly precursor of FIG. 9C can be thermally treated so as to provide the sample layer on the working electrode as shown in FIG. 9D. The thermal treatment removes at least the gelling agent from between adjacent sample locations and can expose the underlying working electrode. As described above, the thermal treatment also removes the gelling agent from the solid layer 46 and can convert the material in each of the solid layers 46 to the desired form.

As noted above, the use of the wetting solvent is optional. Accordingly, the method of FIG. 9A through FIG. 9D can be modified by adding the one or more inks for each sample location directly to the gel precursor layer 40 without adding the wetting solvent. The inks and the gelling precursor combine to form the gel 44 where the sample layer will be formed.

Figure 10:
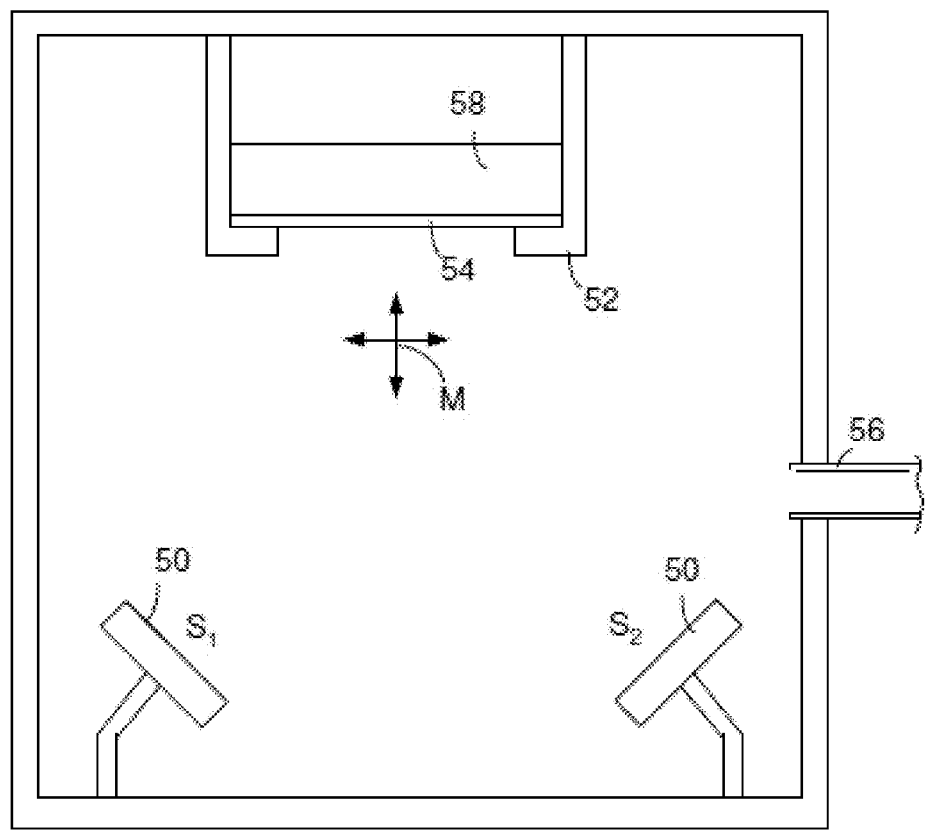
FIG. 10 is a schematic diagram for a cross section of a sputtering chamber.

Physical vapor deposition (PVD) techniques can also be employed to form the samples on the working electrode. Examples of suitable PVD techniques include, but are not limited to, sputtering, evaporation, and pulsed laser deposition. A schematic diagram for a cross section of a sputtering chamber is provided in FIG. 10. The sputtering chamber includes one or more sources 50, a substrate holder 52 configured to hold a substrate 54, and one or more gas inlets 56.

The one or more sources 50 each include a sputtering target and are a source of cations within the chamber. Accordingly, each of the sources 50 can include or consist of one or more metal or semi-metal elements. When a source 50 includes more than one metal element, the different metals can be bonded to one another as occurs in a material such as an alloy. Alternately, the different metals need not be bonded to one another. For instance, the source 50 can include two different metals arranged such that they contact one another at an interface or they fail to contact one another. When the different metals contact one another at an interface, there may be bonding of the different metals at the interface but no bonding away from the interface.

The gas inlets can be used to control the atmosphere within the chamber. For instance, one or more inert (noble) gases and one or more reactive gases can be transported into the chamber through the one or more gas inlets. The reactive gases are a source of anions within the chamber. The cations and anions within the chamber combine to form analytes included in a sample layer that is deposited on the substrate 54.

Two sources 50 are shown in the illustrated sputtering chamber. As shown by the arrows labeled M, the substrate 54 is configured to be moved relative to one or more of the sources and/or one or more of the sources 50 is configured to be moved relative to the substrate 54. A gradient in the ratio of the anions in the analyte can be controlled by the placement of the substrate 54 relative to the one or more sources 50. For instance, the molar percentage of a cation in an analyte on the substrate 54 will be largest closer to the source 50 for that cation and will decrease moving away from that source 50. Accordingly, the ratio of cation A to cation B in the deposited layer can be increased by moving the substrate 54 toward the source of cation A and away from the source of cation B. Further, the degree of the gradient across the substrate 54 can also be controlled by an up and down movement of the substrate 54. For instance, the level of the gradient decreases as the substrate 54 is moved further from the one or more sources 50 but the level of the gradient increases as the substrate 54 is moved closer to the one or more sources 50. Accordingly, moving the substrate 54 upward in the chamber decreases the level of the gradient while downward movement of the substrate 54 increases the level of the gradient.

The above description for controlling the ratio of different cations in the analyte is described in the context of multiple sources 50 within the chamber; however, the same concept can be extended to a single source 50 that includes multiple different metal elements such as an alloy. The sputtering process causes different metals tend to be ejected from the surface of a source 50 at different angles. As a result, the distribution of different cations within the chamber can become uneven. Accordingly, the ratio of cation A to cation B in the deposited layer can be increased by moving the substrate 54 toward the path traveled cation A and away from the path traveled by cation B. As noted above, the degree of the gradient across the substrate 54 can also be controlled by an up and down movement of the substrate 54. For instance, the level of the gradient decreases as the substrate 54 is moved further from the one or more sources 50 but the level of the gradient increases as the substrate 54 is moved closer to the one or more sources 50. Accordingly, moving the substrate 54 upward in the chamber decreases the level of the gradient while downward movement of the substrate 54 increases the level of the gradient.

The ratio of different anions within the analyte can be controlled by controlling the ratio of the reactive gases within the chamber. For instance, increasing the molar ratio of gas A to gas B within the chamber can provide analytes with a higher molar ratio of gas A to gas B. In addition to the reactive gases, the chamber can also include one or more inert gases during deposition of the layer of material. Examples of suitable inert gases include, but are not limited to, the noble gases such as argon.

In some instances, the substrate holder 52 holds a heater 58 that can heat the substrate 54 during deposition of the layer of material. In some instances, the substrate 54 is heated to temperatures greater than 100° C., 500° C., or 800° C. during deposition of the layer of material. Additionally or alternately, the layer of material can be subjected to heat treatment after deposition of the layer of material. The thermal treatment can be performed so as to provide a phase change such as a transition from an amorphous material to a crystalline material or to change from one crystal phase to another crystal phase. Accordingly, the thermal treatment can be performed so as to provide the analyte with the desired phase or form.

An example of a suitable thermal treatment includes, but is not limited to, annealing. An example of annealing that is of particular interest is the process commonly called Rapid Thermal Processing (RTP). The use of Rapid Thermal Processing is desirable because it prevents the undesirable exchange of anions from the deposited layer with the surrounding atmosphere that is associated with other sample fabrication process. In some instances of Rapid Thermal Processing, the deposited layer is heated more than by more than 100 K, 500 K, or 1000 K in a period of time of less than 5 s, 20 s, or 100 s, and, in some instances, the temperature reaches more than 100° C., 500° C., or 1000° C.

Analytes such as metal oxides have become increasingly interesting for use as light absorbers and/or photocatalysts. The physical vapor deposition and optional thermal treatment is suitable for generating metal oxide samples. Further, it is specially suited for generating more complex metal oxides that incorporate more than one metal element and more than one reactive gas. Accordingly, the method can be used to generate analytes that include or incorporate more than two metal elements and more than two components from reactive gasses. For instance, the method is suitable for generating quaternary metal oxides that include more than one reactive gas component such as quaternary oxynitrides. One example of a sample library includes different quaternary oxynitrides where each of the quaternary oxynitrides analytes consists of different ratios of the elements lanthanum, tantalum, oxygen and nitrogen.

The layer of material generated from the above vapor phase deposition (PVD) and optional thermal treatment or the layer of material generated from the method of FIG. 9A through FIG. 9D can be used as a sample layer as disclosed in the context of FIG. 4B. Additionally, the substrate 54 used in the physical vapor deposition (PVD) or from the method of FIG. 9A through FIG. 9D can be used as the associated working electrode. Accordingly, the result of the above physical vapor deposition (PVD) and optional thermal treatment or method of FIG. 9A through FIG. 9D can serve as the working electrode assembly. However, in some instances, it may be desirable for the samples to be discrete from one another as shown in FIG. 1B, FIG. 2B, and FIG. 3B rather than included in a continuous sample layer. In these instances, the layer of material can be divided into independent samples through the use of techniques such as etching, shadow masking, and scribing. When the layer of material includes multiple zones where each zone has a constant or substantially constant analyte composition and the layer of material is divided between zones, each of the zones can serve as a different sample in a working electrode according to FIG. 1A through FIG. 3D. The resulting samples can have a constant composition across the sample. Alternately, if the layer of material is generated to have a smooth and continuous analyte composition gradient across the layer of material, each of the resulting samples can have a composition gradient in one or more directions.

The methods disclosed for generating the samples are capable of generating a wide range of materials. Further, these methods can generate a sample that is both small enough to allow a large number of samples on a substrate while being continuous and without holes over an area of more than 1 $\mu m^2$. Accordingly, in some instances, the samples each occupy an area of a substrate such as the working electrode greater than 1 $\mu m^2$, 1 $mm^2$, or 10 $cm^2$ and/or less than 1 $m^2$, 10 $cm^2$, or 1 $mm^2$. Further, these methods generate samples where the analyte is evenly distributed through the sample. Additionally, the sample is uniformly thick. For instance, these methods can be used to generate samples with an average thickness and a standard deviation from that average thickness of less than 0.1% of the average thickness, 5% of the average thickness, and 50% of the average thickness. Accordingly, these methods are suitable for generating large numbers of high quality samples over areas that exceed 1 $\mu m^2$. The ability to create quality samples over areas larger than 1 $\mu m^2$ can be important because these dimensions are on the order of the wavelength of sunlight.

Although the above methods disclose forming the samples and/or sample layers directly on the working electrode, the samples and/or sample layers can be used to form the samples on other substrates. Additionally or alternately, although the above methods are described in the context of generating samples that include light absorbers, the above methods can be used to generate analytes including, but not limited to, photocatalysts, solid state laser gain media, transparent conducting oxides, dielectrics, and heterogeneous catalysts. Further, the instruments disclosed can be used to screen classes of materials and compounds other than light absorbers. For instance, the instruments disclosed above can be employed to screen classes of materials and compounds such as photocatalysts and solid state laser gain media.

The samples on the working electrodes disclosed above can optionally be generated using technologies and methods other than the methods disclosed above.

Suitable electronics for operating the instrument can include a controller. A suitable controller includes, but is not limited to, a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions attributed to the electronics. A general-purpose processor may be a microprocessor, but in the alternative, the controller may include or consist of any conventional processor, microcontroller, or state machine. A controller may also be implemented as a combination of computing devices, e.g., a combination of a DSP and a microprocessor, a plurality of microprocessors, one or more microprocessors in conjunction with a DSP core, or any other such configuration.

The electronics can optionally include a memory in communication with the controller. The electronics can store data for executing the functions of the electronics in the memory. The memory can be any memory device or combination of memory devices suitable for read and/or write operations.

In some instances, the electronics include a computer-readable medium in communication with the controller. The computer-readable medium can have a set of instructions to be executed by the controller. The controller can read and execute instructions included on the computer-readable medium. The controller executes the instructions such that the electronics perform one or more of the described functions. The computer-readable medium cab be different from the memory or can be the same as the memory. Suitable computer-readable media include, but are not limited to, optical discs such as CDs, magnetic storage diskettes, Zip disks, magnetic tapes, RAMs, and ROMs. Some functions of the electronics may be executed using hardware as opposed to executing these functions in firmware and/or software.

The electronics can optionally include user interfaces such as mice, keyboards, monitors, etc.

The above discussions of the instrument are in the context of the samples being positioned on the working electrode such that the samples are immobilized relative to the working electrode, however, the samples need not be attached to the working electrode. The samples can be located between the working electrode and the counter electrode assembly without being immobilized relative to the working electrode. For instance, the samples can be on a substrate other than the working electrode that is located between the working electrode and the counter electrode assembly.

EXAMPLES

Example 1

Gels were used to generate samples on substrate. Agarose gel precursor (0.5-2% in water) was spun on a glass substrate so as to provide a dry gel precursor layer. The gel precursor layer was less than 1 micron thick but spinning can be adjusted so as to achieve the desired thickness. A liquid mixture of water, diethylene glycol, and diethylene glycol monobutyl ether was used as a wetting solvent. The wetting solvent was added to the gel precursor layer at each of the sample locations where a sample was desired. The wetting solvent was added at a temperature in the range 25-50° C. Inks that included components for the analytes were added to the sample locations in the ratios that would provide the desired analyte at each location. The inks, wetting solvent and gelling agent combined to form a gel at each location. The gels were dried so as to form a solid layer at each of the sample locations. The gels were dried by placing the substrate on a hot plate or in an oven at 100-150° C. The result was then thermally processed at a temperature above 450° C. in air so as to remove any agarose from the solid layer. The thermal processing was performed in an atmosphere that included oxygen in order to generate oxide analytes.

Example 2

Sputtering was used to generate a sample layer on a substrate. The sample layer was generated in a high vacuum PVD chamber with base pressure of 0.5 µTorr evacuated by a cryopump. The size of the chamber is 24-inch diameter by 15-inch height. Six 2-inch KJLC Torus sputtering sources arranged in 6-fold symmetry at the bottom of chamber have independently controlled shutters and in-situ tilt assemblies, above which the substrate platen with heating in the range of 25-800° C. is installed on a rotation and translation stage allowing to varying the source-to-substrate distance. A DC or RF power supply is applied to each source depending on the type of the material being deposited. The relative flow rates of Ar and $N_2$ gases are controlled using mass flow controller with total pressure measured using a capacitance manometer. Control of $O_2$ pressure at the 1 µTorr level is realized by fine adjusting a variable leak value and measured by wide range vacuum gauge. The deposition rate around the substrate center of each material can be measured by the quartz crystal thickness monitor.

In the PVD chamber, La (99.9%) and Ta (99.95%) targets were used. They were both tilted 24° towards the chamber center. A substrate of thermalized $SiO_2$ layer (~170 nm) on Si(001) is positioned at z=3.6 above the targets. The working atmosphere is composed by Ar (4.47 mTorr), $N_2$ (1.5 mTorr) and $O_2$ (0.03 mTorr). The total working gas pressure was kept constant at 6 mTorr. The La and Ta targets were pre-cleaned at Ar pressure of 6 mTorr for 10 minutes to get rid of the possible poison and contaminations on the target surfaces. In order to obtain the desired mole ratio of La to Ta to be 1 around the substrate center, the power applied on each source was adjusted according to the measured corresponding deposition rate. The power applied to the La and Ta sources was 100 W RF and 60 W DC, respectively. The deposition lasted 2 hours. This as-deposited La—Ta—O—N film is also annealed at 900° C. for 30 seconds by RTP under flowing of $N_2$. A thin film that included La, Ta, O, and N in various molar rations and with various crystalline phases was observed by energy dispersive x-ray spectroscopy and x-ray diffraction.

Other embodiments, combinations and modifications of this invention will occur readily to those of ordinary skill in the art in view of these teachings. Therefore, this invention is to be limited only by the following claims, which include all such embodiments and modifications when viewed in conjunction with the above specification and accompanying drawings.

The invention claimed is:

1. An instrument, comprising:
    samples located between a working electrode and a counter electrode assembly comprising a plurality of counter electrodes, the samples each including one or more analytes, each of the analytes including a semiconductor, a distance between the working electrode and the counter electrode assembly being less than 10 mm, and
    one or more light sources that each act as a source of one or more light beams that are each incident on one or more of the samples.
2. The instrument of claim 1, wherein the distance between the working electrode and the counter electrode assembly is less than 5 mm.
3. The instrument of claim 1, further comprising:
    an electrolyte between the working electrode and the counter electrode assembly, the electrolyte including a redox couple.
4. The instrument of claim 3, wherein the redox couple undergoes a reversible electrochemical oxidation with an exchange current density of at least 1 mA cm$^{-2}$ for at least one of the counter electrodes of the plurality of counter electrodes.
5. The instrument of claim 3, wherein the electrolyte is in direct physical contact with the samples and the working electrode.
6. The instrument of claim 5, wherein the electrolyte and the samples exclude catalysts.
7. The instrument of claim 1, wherein the working electrode is optically transparent and the one or more light beams pass through the working electrode before being incident on the samples.
8. The instrument of claim 1, wherein the counter electrode assembly includes a single counter electrode.
9. The instrument of claim 1, further comprising electronics that generate a value for a rate parameter that indicates a level of an electrical current through one of the counter electrodes.
10. The instrument of claim 9, wherein the electronics correct the rate parameter for effects of dark current.
11. The instrument of claim 10, further comprising electronics that generate a value for a conversion parameter that indicates a level of photocurrent through one of the samples upon which one of the light beams is incident.
12. The instrument of claim 10, wherein the electronics correct the conversion parameter for effects of a parasitic reaction that occurs in the electrolyte.

13. The instrument of claim 1, wherein the samples are attached to the working electrode such that the samples are immobilized relative to the working electrode.

14. The instrument of claim 1, wherein at least a portion of the samples each includes one or more metal elements and oxygen.

\* \* \* \* \*